(12) United States Patent
Sumiya

(10) Patent No.: US 10,136,806 B2
(45) Date of Patent: Nov. 27, 2018

(54) IMAGE DISPLAY METHOD, IMAGE DISPLAY APPARATUS, AND STORAGE MEDIUM

(71) Applicant: CANON KABUSHIKI KAISHA, Tokyo (JP)

(72) Inventor: Toshiharu Sumiya, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/408,749

(22) Filed: Jan. 18, 2017

(65) Prior Publication Data

US 2017/0209037 A1 Jul. 27, 2017

(30) Foreign Application Priority Data

Jan. 21, 2016 (JP) ................................. 2016-009544

(51) Int. Cl.
| | | |
|---|---|---|
| *A61B 3/14* | (2006.01) | |
| *A61B 3/00* | (2006.01) | |
| *A61B 3/10* | (2006.01) | |
| *A61B 3/12* | (2006.01) | |
| *G02B 26/10* | (2006.01) | |

(52) U.S. Cl.
CPC .......... *A61B 3/0058* (2013.01); *A61B 3/0025* (2013.01); *A61B 3/102* (2013.01); *A61B 3/1025* (2013.01); *A61B 3/1233* (2013.01); *A61B 3/14* (2013.01); *G02B 26/101* (2013.01)

(58) Field of Classification Search
CPC .......... A61B 3/14; A61B 3/0025; A61B 3/12; A61B 3/102; A61B 3/0058

USPC .................................................. 351/200–246
See application file for complete search history.

(56) References Cited

U.S. PATENT DOCUMENTS

| | | | |
|---|---|---|---|
| 9,520,154 B2 * | 12/2016 | Lee ...................... | H04N 5/2624 |
| 2012/0189066 A1 * | 7/2012 | Kameyama ........... | G06T 3/4053 |
| | | | 375/240.26 |
| 2013/0342718 A1 * | 12/2013 | Williams .............. | H04N 5/2356 |
| | | | 348/222.1 |
| 2014/0221827 A1 | 8/2014 | Motaghiannezam et al. | |
| 2015/0168127 A1 * | 6/2015 | Takeno .............. | G01B 9/02091 |
| | | | 356/479 |
| 2016/0143529 A1 * | 5/2016 | Miyashita .............. | A61B 3/152 |
| | | | 351/208 |

OTHER PUBLICATIONS

Makita, Shuichi et al., "Optical Coherence Angiography", Optics Express, Aug. 21, 2016, vol. 14, No. 17, pp. 7821-7840.

(Continued)

*Primary Examiner* — Mohammed Hasan
(74) *Attorney, Agent, or Firm* — Fitzpatrick, Cella, Harper & Scinto

(57) ABSTRACT

An image display method includes acquiring a first image of a fundus within a first area of an eye to be inspected, acquiring interference signal sets corresponding to a plurality of frames, which are acquired with an intention to acquire the same cross section, for a plurality of different cross sections, generating, based on the interference signal sets corresponding to the plurality of frames, a motion contrast image of the fundus within a second area included in the first area, and superimposing, for display, information acquired from a portion of the motion contrast image of the fundus onto a corresponding position of the first image of the fundus.

36 Claims, 13 Drawing Sheets

(56) References Cited

OTHER PUBLICATIONS

An, Lin et al.,"Optical microangiography provides correlation between microstructure and microvasculature of optic nerve head in human subjects", Journal of Biomedical Optics, Nov. 2012, vol. 17(11), pp. 116018-0-116018-6.

Fingler, Jeff et al.,"Mobility and transverse flow visualization using phase variance contrast with spectral domain optical coherence tomography", Optics Express, Oct. 1, 2007, vol. 15, No. 20, pp. 12636-12653.

Mariampillai, Adrian et al.,"Optimized speckle variance OCT imaging of microvasculature", Optics Letters, Apr. 15, 2010, vol. 35, No. 8, pp. 1257-1259.

* cited by examiner

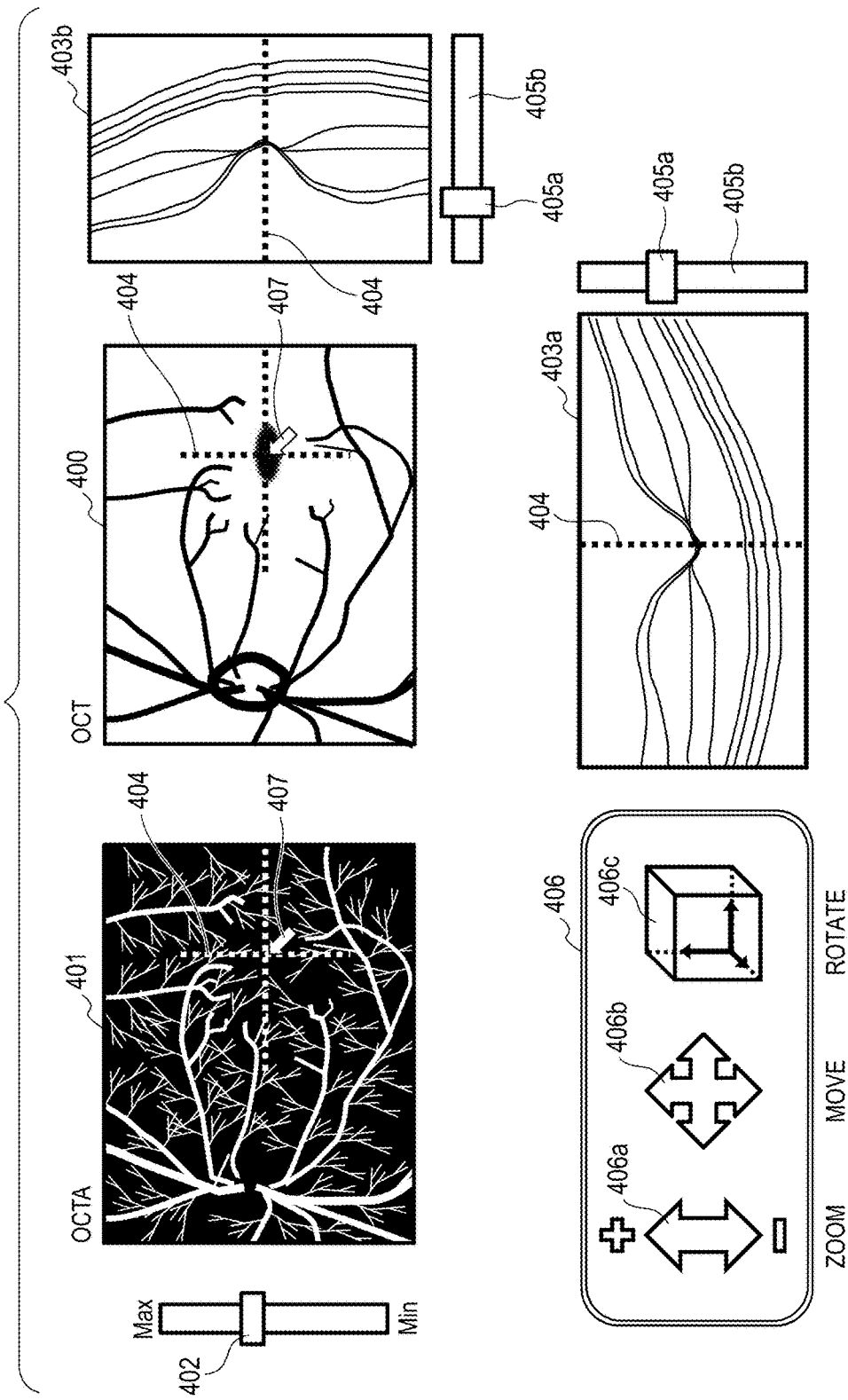

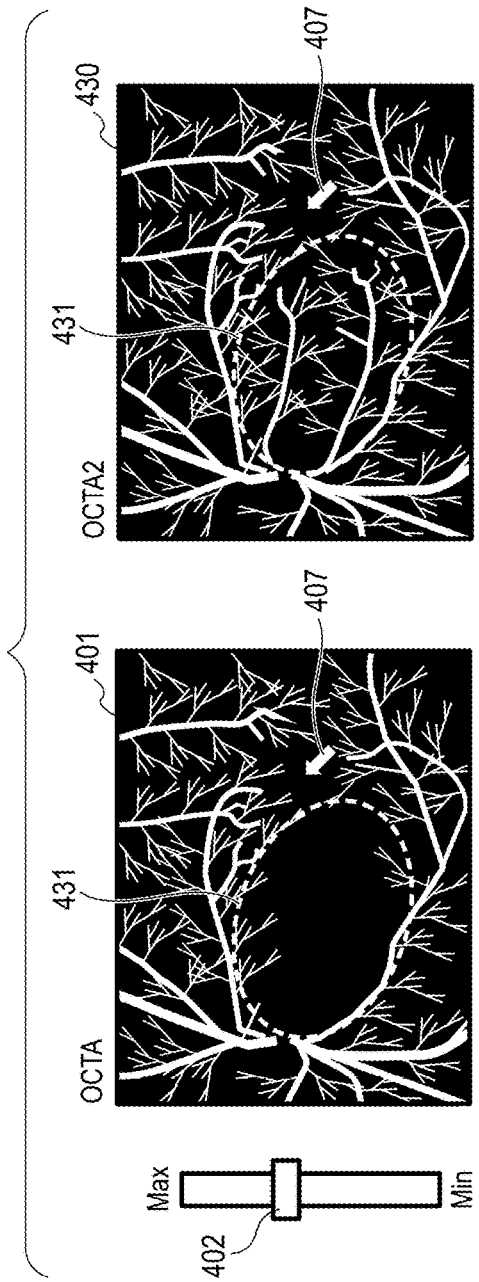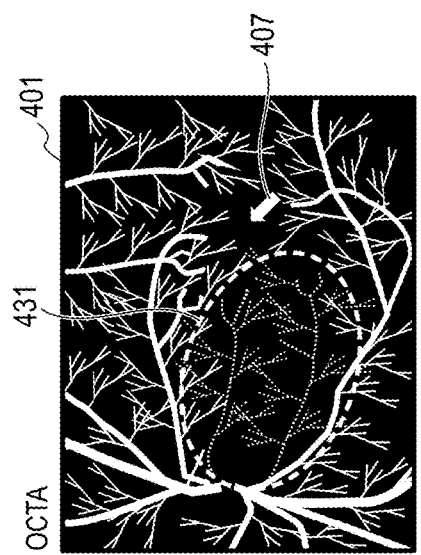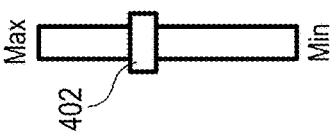
FIG. 18A
FIG. 18B

IMAGE DISPLAY METHOD, IMAGE DISPLAY APPARATUS, AND STORAGE MEDIUM

BACKGROUND

Field

This disclosure relates to an image display method, an image display apparatus, and a storage medium.

Description of the Related Art

As a method of acquiring a tomographic image of an object to be measured, e.g., a living body, in a non-destructive and non-invasive manner, optical coherence tomography (hereinafter referred to as "OCT") has been put into practical use. OCT is widely used particularly in the field of ophthalmology in order to acquire a tomographic image of a retina in a fundus of an eye to be inspected for ophthalmologic diagnosis of the retina, or the like.

In OCT, light reflected from the object to be measured and light reflected from a reference mirror are caused to interfere with each other, and time dependence or wavenumber dependence of an intensity of the interference light is analyzed, to thereby acquire a tomographic image. As apparatus for acquiring such an optical coherence tomographic image, there are known a time domain OCT apparatus, a spectral domain OCT apparatus, and a swept source OCT apparatus. The time domain OCT apparatus is configured to acquire depth information on the object to be measured by changing a position of the reference mirror. The spectral domain optical coherence tomography (SD-OCT) apparatus using a broadband light source is configured to split interference light into light beams having different wavelengths with a spectroscope to acquire depth information on the object to be measured. The swept source optical coherence tomography (SS-OCT) apparatus is configured to use a wavelength-tunable light source apparatus capable of changing an oscillation wavelength. The SD-OCT and the SS-OCT are collectively referred to as "Fourier domain optical coherence tomography (FD-OCT)".

In recent years, there has been proposed simulated angiography using FD-OCT, which is referred to as "OCT angiography (OCTA)" (Makita et al., "Optical Coherence Angiography," Optics Express, 14(17), 7821-7840 (2006)). In fluorescence angiography, which is general angiography in contemporary clinical medicine, injection of a fluorescent dye (e.g., fluorescein or indocyanine green) into a body is required, and a vessel through which the fluorescent dye passes is displayed two-dimensionally. Meanwhile, OCTA enables non-invasive and simulated imaging of vessels, and enables three-dimensional display of a network of a blood flow region. Further, OCTA is attracting attention because OCTA provides a higher resolution as compared with fluorescence angiography, which enables a minute vessel or blood flow of the fundus to be drawn.

There have been proposed a plurality of methods for OCTA, which differ in blood flow detection method. For example, in "An et al. 'Optical microangiography provides correlation between microstructure and microvasculature of optic nerve head in human subjects,' J. Biomed. Opt. 17, 116018 (2012)", there is proposed a method involving extracting only a signal that is changing in time from OCT signals, to thereby obtain an OCT signal due to a blood flow. In "Fingler et al. 'Mobility and transverse flow visualization using phase variance contrast with spectral domain optical coherence tomography' Optics Express. Vol. 15, No. 20. pp. 12636-12653 (2007)", there is proposed a method using a phase variance due to a blood flow. In each of "Mariampillai et al., 'Optimized speckle variance OCT imaging of microvasculature,' Optics Letters 35, 1257-1259 (2010)" and U.S. Patent Application Publication No. 2014/221827, there is proposed a method using an intensity variance due to a blood flow.

However, in the above-mentioned OCTA, a blood flow region can be acquired in detail, and hence, an inspector may have difficulty in identifying a connection of a specific vessel of interest and how the specific vessel extends. Further, an image relating to the blood flow region acquired through the above-mentioned OCTA and an image relating to the structure information acquired through OCT are acquired as independent and separate images. Thus, in actual diagnosis, the inspector needs to compare those images with each other alternately. However, because the detailed blood flow region acquired through OCTA is displayed in detail, its correspondence to structure information on the eye to be inspected that is acquired from an OCT intensity image, a fundus photograph, or the like, is difficult to understand.

This disclosure has been made in view of the above-mentioned circumstances, and it is an object of this disclosure to facilitate understanding of correspondence between an image relating to a blood flow region acquired through OCTA and structure information acquired through OCT, or the like.

In order to solve the above-mentioned problem, one aspect of the present invention is an image display method comprising the steps of acquiring a first image within a first area of an object to be inspected, acquiring interference signal sets corresponding to a plurality of frames, which are acquired with an intention to acquire the same cross section, for a plurality of different cross sections, generating, based on the interference signal sets corresponding to the plurality of frames, a motion contrast image within a second area included in the first area, and superimposing, for display, information acquired from a part of the motion contrast image onto a corresponding position of the first image.

According to this disclosure, understanding of the correspondence between the image relating to the blood flow region acquired through OCTA and the structure information acquired through OCT, or the like, can be facilitated.

Further features of the present invention will become apparent from the following description of exemplary embodiments with reference to the attached drawings.

BRIEF DESCRIPTION OF THE DRAWINGS

FIG. 8 is a diagram for illustrating an example of a display screen according to the first embodiment.

FIG. 18A and FIG. 18B are each a diagram for illustrating an example of a display screen according to a fourth embodiment of this disclosure.

DESCRIPTION OF THE EMBODIMENTS

Embodiments of this disclosure are described below in detail with reference to the drawings. The following embodiments are not to limit this disclosure laid down in the appended claims, and not all combinations of features described in the following embodiments are indispensable to the solutions of this disclosure.

Further, herein, an OCT signal displayed as an image is referred to as "intensity image". Further, a signal that is changing in time among the OCT signals and is displayed as an image is referred to as "motion contrast image", a pixel value of the motion contrast image is referred to as "motion contrast", and a data set of the motion contrast image is referred to as "motion contrast data".

(First Embodiment)

In a first embodiment of this disclosure, an example is described in which a tomographic image is generated from a three-dimensional optical interference signal acquired through imaging, and a motion contrast is calculated to acquire three-dimensional blood flow region information.

[Configuration of Entire Image Forming Apparatus]

Figure 1:
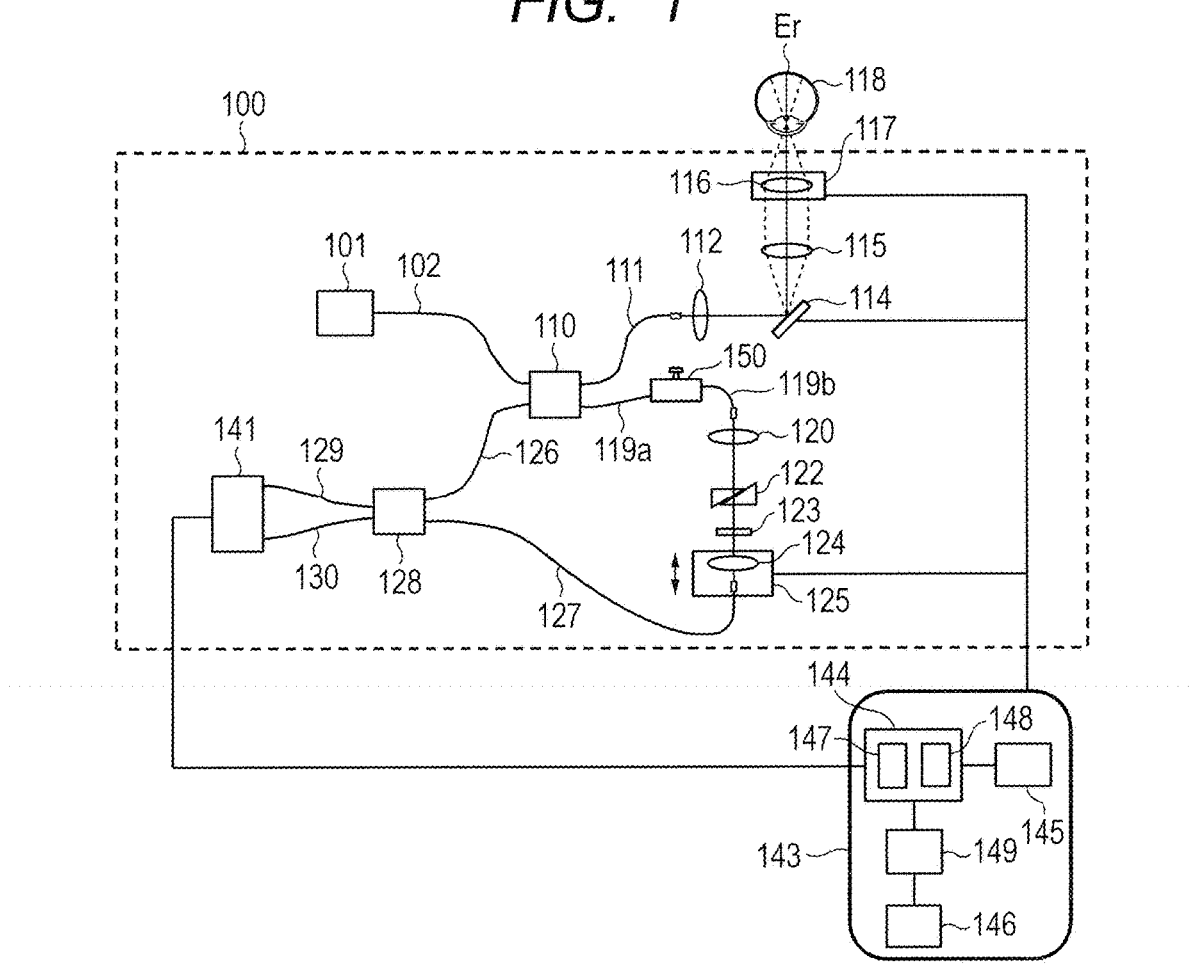
FIG. 1 is a diagram for illustrating an overview of an entire configuration of an apparatus according to a first embodiment of this disclosure.

FIG. 1 is a diagram for illustrating a configuration example of an image forming method and apparatus using optical coherence tomography according to an embodiment of this disclosure. The image forming method and apparatus include an OCT apparatus 100 serving as an optical coherence tomography acquisition unit configured to acquire an optical coherence tomography signal, and a control portion 143. For example, the SD-OCT apparatus and the SS-OCT apparatus described above are applicable to this disclosure as the OCT apparatus. In the embodiment described below, a configuration of a case where the OCT apparatus is the SS-OCT apparatus is described.

<Configuration of OCT Apparatus 100>

Now, a configuration of the OCT apparatus 100 is described with reference to FIG. 1.

A light source 101 is a swept source (hereinafter referred to as "SS") light source, and is configured to emit light while sweeping a wavelength of the light with a sweeping central wavelength of 1,050 nm and a sweeping width of 100 nm, for example.

Light emitted from the light source 101 is guided to a beam splitter 110 via an optical fiber 102, and the light is divided into measuring light (also referred to as "OCT measuring light") and reference light (also referred to as "reference light corresponding to OCT measuring light"). The beam splitter 110 divides the light at a ratio of 90 (reference light):10 (measuring light). The measuring light obtained by division is emitted to a measurement optical path via an optical fiber 111. On the measurement optical path, in order from the optical fiber 111 to an eye to be inspected 118, a collimator lens 112, a galvano scanner 114, a scan lens 115, and a focus lens 116 are arranged.

The measuring light emitted to the measurement optical path is formed into collimated light by the collimator lens 112. The measuring light formed into the collimated light enters the eye to be inspected 118 via the galvano scanner 114, the scan lens 115, and the focus lens 116, which are configured to scan the measuring light on a fundus Er of the eye to be inspected 118. The galvano scanner 114 is described here as a single mirror, but is actually formed of two galvano scanners (not shown), e.g., an X-axis scanner and a Y-axis scanner, so as to raster-scan the fundus Er of the eye to be inspected 118.

The focus lens 116 is fixed onto a stage 117, and when the stage 117 moves in an optical axis direction, focus can be adjusted with the focus lens 116. The galvano scanner 114 and the stage 117 are controlled by a signal acquisition control portion 145 described later, to thereby be able to scan the measuring light within a desired range of the fundus Er of the eye to be inspected 118 (also referred to as "acquisition range of tomographic image", "acquisition position of tomographic image", and "irradiation position of measuring light").

Although not described in detail in this embodiment, it is desired that the OCT apparatus 100 be provided with a tracking function of detecting movement of the fundus Er to cause the mirrors of the galvano scanner 114 to scan the light while following the movement of the fundus Er. A general technology can be used to perform a tracking method, and the tracking method may be performed in real time, or may be performed in post processing.

As a method of acquiring a fundus image in order to detect the movement of the fundus Er, there is given, for example, a method using a scanning laser ophthalmoscope (SLO). In this method, an image of the fundus Er within a plane perpendicular to an optical axis (fundus surface image) is acquired over time through use of SLO to extract a characteristic portion within the image, e.g., a portion in which a vessel branches. How the characteristic portion within the acquired two-dimensional image has moved is calculated as a moving amount of the fundus Er, and the calculated moving amount is fed back to the galvano scanner 114. In this manner, real-time tracking can be performed.

As described above, the measuring light enters the eye to be inspected 118 via the focus lens 116 fixed onto the stage 117, and is focused onto the fundus Er by the focus lens 116. The measuring light that has irradiated the fundus Er is reflected and scattered by each retinal layer and returns to the beam splitter 110 via the measurement optical path. The return light of the measuring light that has entered the beam splitter 110 passes through an optical fiber 126 to enter a beam splitter 128.

Meanwhile, the reference light obtained by division by the beam splitter 110 is emitted to a reference optical path via an optical fiber 119a, a polarization controller 150, and an optical fiber 119b. On the reference optical path, in order from the optical fiber 119b, a collimator lens 120, a dispersion compensation glass 122, an ND filter 123, and a collimator lens 124 are arranged.

The reference light emitted from the optical fiber 119b is formed into collimated light by the collimator lens 120. The polarization controller 150 is capable of changing polarization of the reference light to a desired polarization state. The reference light enters an optical fiber 127 via the dispersion compensation glass 122, the ND filter 123, and the collimator lens 124. One end of the collimator lens 124 and one end of the optical fiber 127 are fixed onto a coherence gate stage 125, and the collimator lens 124 and other members are controlled by the signal acquisition control portion 145 described later so as to be driven in an optical axis direction depending on the difference in axial length among subjects to be examined, or the like. Although an optical path length of the reference light is changed in this embodiment, an optical path length of the measuring light may be changed as long as the difference in length between the optical path of the measuring light and the optical path of the reference light can be changed.

The reference light that has passed through the optical fiber 127 enters the beam splitter 128. In the beam splitter 128, the above-mentioned return light of the measuring light and the reference light are coupled to become interference light, and the interference light is divided into two light beams. The interference light is divided into interference light beams having phases inverted to each other (hereinafter expressed as "positive component" and "negative component"). The positive component of the interference light obtained by division passes through an optical fiber 129 to enter one of input ports of a detector 141. Meanwhile, the negative component of the interference light passes through an optical fiber 130 to enter the other input port of the detector 141. The detector 141 serves as a differential detector, and when two interference signals having phases inverted to each other by 180° are input, removes a DC component and outputs only an interference component.

The interference signals detected by the detector 141 are output as an electrical signal corresponding to intensity of light, and the electrical signal is input to a signal processing portion 144, which is an example of a tomographic image generation portion.

<Configuration of Control Portion 143>

The control portion 143 for controlling the image forming apparatus is described.

The control portion 143 includes the signal processing portion 144, the signal acquisition control portion 145, a display portion 146, and a display control portion 149. Further, the signal processing portion 144 includes an image generation portion 147 and a map generation portion 148. The image generation portion 147 has a function of generating a luminance image and a motion contrast image based on the electric signal sent thereto, and the map generation portion 148 has a function of generating layer information (segmentation of a retina) based on the luminance image.

The signal acquisition control portion 145 is configured to control the stage 117, the coherence gate stage 125, and other members as described above. The signal processing portion 144 is configured to generate an image, analyze the generated image, and generate visible information on an analysis result based on the signal output from the detector 141.

The image generated by the signal processing portion 144 and its analysis result are sent to the display control portion 149, and the display control portion 149 displays the sent image and analysis result on a display screen of the display portion 146. The display portion 146 is a display, e.g., a liquid crystal display. Image data generated by the signal processing portion 144 may be transmitted to the display portion 146 in a wired or wireless manner after being sent to the display control portion 149. Further, although the display portion 146 and other portions are included in the control portion 143 in this embodiment, this disclosure is not limited thereto. The display portion 146 and other portions may be provided separately from the control portion 143, and may be, for example, a tablet computer, which is an example of a device that can be carried around by a user. In this case, it is preferred that the display portion be provided with a touch panel function so that movement of a display position of an image, enlargement/reduction of the image, change of an image to be displayed, other such operations can be performed on a touch panel.

[Scan Pattern]

<Mode of Scanning Measuring Light in OCT Apparatus>

Now, a mode of scanning the measuring light in the OCT apparatus is described. As described above, the interference light is acquired based on the return light of the measuring light that has been radiated onto an arbitrary point on the fundus of the eye to be inspected 118 and the corresponding reference light. The signal processing portion 144 processes the electrical signal corresponding to the intensity of the interference light detected by the detector 141 to acquire image data at the arbitrary point in a depth direction. A process of acquiring information on a layer at a given point on the eye to be inspected 118 has been described above. Acquisition of the information on a layer in the depth direction of the eye to be inspected 118 is referred to as "A-scan".

Further, acquisition of the information on a layer of the eye to be inspected 118 in a direction orthogonal to that of the A-scan, that is, acquisition of information on a plurality of layers in the above-mentioned depth direction in a scan direction for acquiring a two-dimensional image is referred to as "B-scan". Still further, acquisition of information on the plurality of layers in the depth direction in a scan direction orthogonal to both of the scan directions of the A-scan and the B-scan is referred to as "C-scan". When a two-dimensional raster scan is performed on a fundus surface in order to acquire a three-dimensional tomographic image, a direction of a high-speed scan is referred to as "B-scan direction", and a direction of a low-speed scan in which scans are performed while lining up B-scans in a direction orthogonal to the B-scan direction is referred to as "C-scan direction". A two-dimensional tomographic image is acquired by performing the A-scan and the B-scan, and the three-dimensional tomographic image is acquired by performing the A-scan, the B-scan, and the C-scan. The B-scan and the C-scan are performed by changing the irradiation position of the measuring light with the above-mentioned galvano scanner 114.

As described above, the galvano scanner 114 is formed of the X-axis scanner and the Y-axis scanner (not shown), each of which is formed of a deflecting mirror arranged to have a rotational axis orthogonal to that of the other deflecting mirror. For example, the X-axis scanner is configured to scan the measuring light on the fundus Er in an X-axis direction, and the Y-axis scanner is configured to scan the measuring light on the fundus Er in a Y-axis direction. The X-axis direction and the Y-axis direction are directions that are perpendicular to an axial direction of an eyeball and are perpendicular to each other.

Further, a line scan direction for the B-scan or the C-scan and the X-axis direction or the Y-axis direction do not need to match. Accordingly, the line scan direction for the B-scan or the C-scan may be determined appropriately depending on a two-dimensional or three-dimensional tomographic image desired to be taken.

<Mode of Scanning Measuring Light According to This Embodiment>

Figure 2:
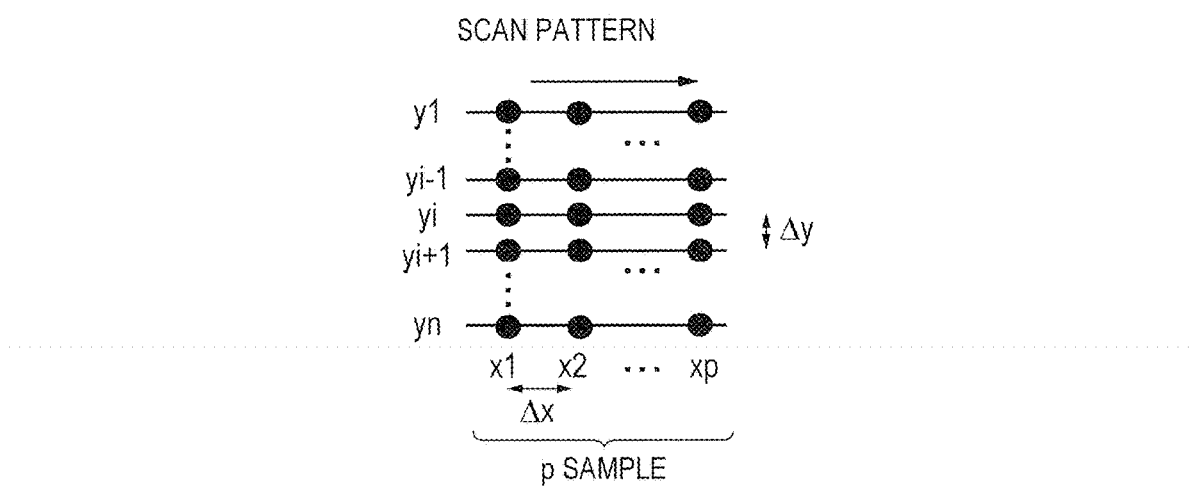
FIG. 2 is a diagram for illustrating an example of a scan pattern according to the first embodiment.

In OCTA, in order to measure a change with time of the OCT interference signal due to a blood flow, measurement needs to be performed a plurality of times at the same position. In this embodiment, while repeating the B-scan (scan in the X-axis direction) at the same position m times, the OCT apparatus performs a scan of moving a scan position to n y-positions (positions to which the irradiation position of the measuring light is moved in the Y-axis direction). A specific scan pattern is illustrated in FIG. 2. As illustrated in FIG. 2, in this embodiment, the OCT apparatus repeats the B-scan m times at each of the n y-positions y1 to yn on a fundus plane.

In this case, as the value of m becomes larger, the number of times of measurement at the same position also increases, and hence an accuracy of detecting the blood flow increases. Meanwhile, the scan time increases, and hence there arise problems in that a motion artifact occurs in an image due to movement of an eye (involuntary eye movement during fixation) during a scan and in that burden on the subject to be examined increases. In this embodiment, m is set to 4 in consideration of the balance between the two. The control portion 143 may be configured to automatically change m depending on an A-scan speed of the OCT apparatus and motion analysis of a fundus surface image of the eye to be inspected 118.

Further, in FIG. 2, p represents the number of samples of the A-scan in one B-scan. In other words, in one B-scan, the A-scan is performed at each of positions x1 to xp, and the size of the plane image is determined based on p×n. As the value of p×n becomes larger, a wider range can be scanned as long as a measurement pitch is the same. However, the scan time increases, and hence the above-mentioned problems in the motion artifact and the increase in the burden on the subject to be examined arise. In this embodiment, n and p are each set to 300 in consideration of the balance between the two. The values of n and p may be freely changed as necessary.

Further, $\Delta x$ of FIG. 2 represents an interval (x-pitch) between adjacent x-positions, and $\Delta y$ of FIG. 2 represents an interval (y-pitch) between adjacent y-positions. In this embodiment, each of the x-pitch and the y-pitch is determined as ½ of a beam spot diameter of the light radiated to the fundus, specifically, 10 µm. When each of the x-pitch and the y-pitch is set to ½ of the beam spot diameter on the fundus, the image to be generated can be formed with high resolution. Even when each of the x-pitch and the y-pitch is set to be smaller than ½ of the beam spot diameter on the fundus, an effect of further increasing the resolution of the image to be generated is small.

In contrast, when each of the x-pitch and the y-pitch is set to be larger than ½ of the beam spot diameter on the fundus, the resolution deteriorates, but the image of a wider range can be acquired with a small data size. However, each of the x-pitch and the y-pitch may be freely changed depending on a clinical requirement.

A scan range in this embodiment is p×$\Delta x$=3 mm in the X-axis direction and n×$\Delta y$=3 mm in the Y-axis direction.

<Mode of Acquiring OCT Interference Signal and OCTA Signal>

The OCT interference signal and an OCTA signal may be acquired in the same step, or may be acquired in different steps. In the following, a case when the OCT interference signal and the OCTA signal are acquired in the same step is described. When those signals are acquired in the same step, the signal acquisition control portion 145 measures the same position a plurality of times during the scan with the measuring light, to thereby acquire interference signal sets corresponding to a plurality of frames to be used when forming the three-dimensional tomographic image. In this case, the signal acquisition control portion 145 functions as a signal acquiring unit. The interference signal set is a set of interference signals acquired through the above-mentioned one B-scan, and means a set of interference signals from which one frame of the tomographic image of the B-scan can be formed. Further, the eye to be inspected performs involuntary eye movement during fixation at any time, and hence even when an attempt is made to form an image of the same cross section of the eye to be inspected by acquiring the interference signal sets corresponding to the plurality of frames through a plurality of times of scans at the same position on the eye to be inspected, it is difficult to accurately acquire the same cross section in actual cases. Accordingly, the interference signal sets corresponding to the plurality of frames described here are understood as the interference signal sets corresponding to the plurality of frames, which are acquired with an intention to acquire the same cross section. As another example, the above-mentioned interference signal set is the interference signal sets corresponding to the plurality of frames acquired by scanning, with a scan unit exemplified by the galvano scanner 114 configured to scan the measuring light on the fundus, the measuring light repeatedly along the same scan line (B-scan line).

The signal processing portion 144 processes the interference signal sets to calculate the OCT interference signal and the OCTA signal. Through use of the interference signal sets acquired in the same step, the pixels of the OCT intensity image and the OCTA motion contrast image can be formed at the same position. In other words, in this embodiment, the interference signal set to be used for generating the OCT intensity image is included in the interference signal sets corresponding to the plurality of frames, which are acquired in order to generate the OCTA motion contrast image. Further, the OCT intensity image to be displayed as a two-dimensional image may be acquired by averaging (superimposing) two or more interference signal sets among the above-mentioned acquired interference signal sets corresponding to the plurality of frames, that is, two frames. With this configuration, random noises contained in the interference signal sets are averaged, and hence the noise of the intensity image can be reduced. In this case, the signal processing portion 144 functions as a motion contrast image generation unit configured to generate the motion contrast image through use of corresponding pieces of pixel data of the frames in the interference signal sets corresponding to the plurality of frames forming the same cross section.

Next, a case when the OCT interference signal and the OCTA signal are acquired in different steps is described. When those signals are acquired in different steps, for example, the signal acquisition control portion 145 causes the OCT apparatus 100 to acquire the OCTA signal after acquiring the OCT interference signal. In a scan pattern at the time of acquisition of the OCT interference signal, the number of times of repetition, the pitch, and other values that are suited to the scan pattern are used. For example, the OCT interference signal does not necessarily need to be acquired by repeating the B-scan m times. Further, the scan range does not need to be the same for both of the acquisition of the OCT interference signal and the acquisition of the OCTA signal. Therefore, as long as the scan time is the same, the OCT interference signal can be acquired with a wider range as a first predetermined range. Further, when the signals are acquired in different steps, for example, those signals can be used in the following manner: while a wide range is observed with the OCT three-dimensional tomographic image, the OCTA signal is acquired in detail only in a predetermined area of interest as a second predetermined range included in the first predetermined range.

Figure 3:
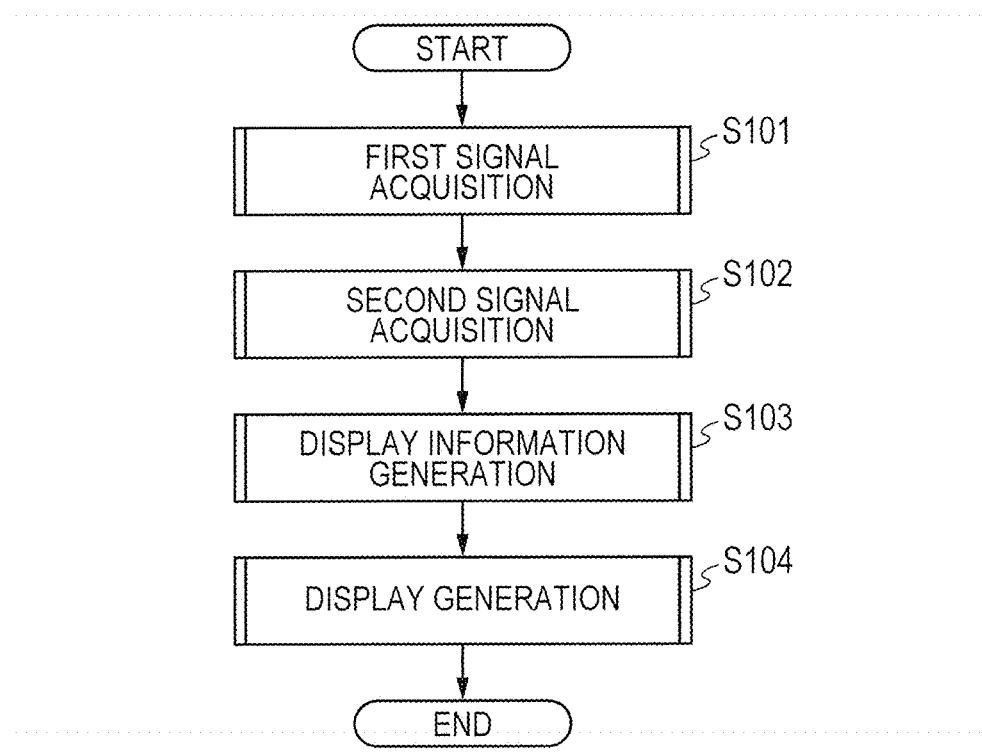
FIG. 3 is a flowchart for illustrating an entire processing procedure for image generation according to the first embodiment.

Next, referring to a flowchart of FIG. 3, a specific processing procedure of the image forming method or the image display method according to this embodiment is described. A detailed description of each processing step illustrated in the flow is given later. Referring to FIG. 3, an example in which the OCT interference signal and the OCTA signal are acquired in different steps is described.

In Step S101, which is a first signal acquisition step, that is, a step of acquiring an object-to-be-inspected image to be displayed as a two-dimensional image, the signal acquisition control portion 145 controls the OCT apparatus 100 to acquire the optical coherence tomography signal.

In Step S102, which is a second signal acquisition step, that is, a signal acquisition step, the signal acquisition control portion 145 controls the OCT apparatus 100 to acquire the optical coherence tomography signals corresponding to the plurality of frames. More specifically, the interference signal sets corresponding to the plurality of frames, which are based on the measuring light controlled to scan the same position in a sub-scan direction a plurality of times, are acquired. Further, this operation is executed a plurality of times while shifting the scan position in the sub-scan direction in order to acquire the interference signal sets from a plurality of different cross sections, to thereby acquire the interference signal sets sufficient for forming a three-dimensional tomographic image.

In Step S103, which is an intensity image (display information) generation step, the control portion 143 calculates three-dimensional tomographic image data of the eye to be inspected 118 based on the optical coherence tomography signal acquired in the first signal acquisition step, to thereby generate an intensity image. Further, the control portion 143 calculates three-dimensional motion contrast data based on the optical coherence tomography signals corresponding to the plurality of frames acquired in the second signal acquisition step, to thereby generate a three-dimensional motion contrast image.

In Step S104, which is a display generation step, the control portion 143 generates and displays display information based on the intensity image and the three-dimensional motion contrast image. In response to an inspector's operation, the control portion 143 reconstructs and redisplays the display information. A detailed description of the reconstruction processing is given later.

After the above-mentioned steps are executed, the processing procedure of the image forming method according to this embodiment is brought to an end.

That is, in this embodiment, in Step S101, which is the first signal acquisition step, a surface image of the fundus (first image) in a first area of the fundus Er (object to be inspected) of the eye to be inspected 118 is acquired. In this embodiment, the first image is generated based on the interference signal set acquired from the first area. At this time, the interference signal set may be selected for use from among the interference signal sets corresponding to the plurality of frames acquired in Step S102. In this case, as described later, the first image is generated by superimposing, in the depth direction, pieces of data of the three-dimensional tomographic image of the object to be inspected acquired from the interference signal sets corresponding to the plurality of frames.

In Step S102, which is the second signal acquisition step, the interference signal sets corresponding to the plurality of frames, which are acquired with an intention to acquire the same cross section, are acquired for a plurality of different cross sections. From the acquired interference signal sets corresponding to the plurality of frames, in Step S103, which is the display information generation step, the motion contrast image based on those signals in a second area included in the first area on the fundus Er is generated. Further, in Step S104, which is the display generation step, information acquired from a part of the motion contrast image is superimposed onto a corresponding position of the first image exemplified by the above-mentioned fundus surface image, and the resultant image is displayed.

It is preferred that, in the superimposition of images, position alignment be performed between data of the three-dimensional tomographic image of the object to be inspected and three-dimensional image data that is based on the interference signal set used for generating the motion contrast image. In this case, as described in this embodiment, information on vessels of the object to be inspected can be given as the information acquired from a part of the motion contrast image, and examples of the information include a state representing a connection state of vessels as described later. Further, in this case, the information on vessels may be extracted not only from the motion contrast image but also from the first image, and the extracted information on vessels may be superimposed for display onto a corresponding position of one of the images from which the information is not extracted.

[Interference Signal Acquisition Procedure]

Figure 4:
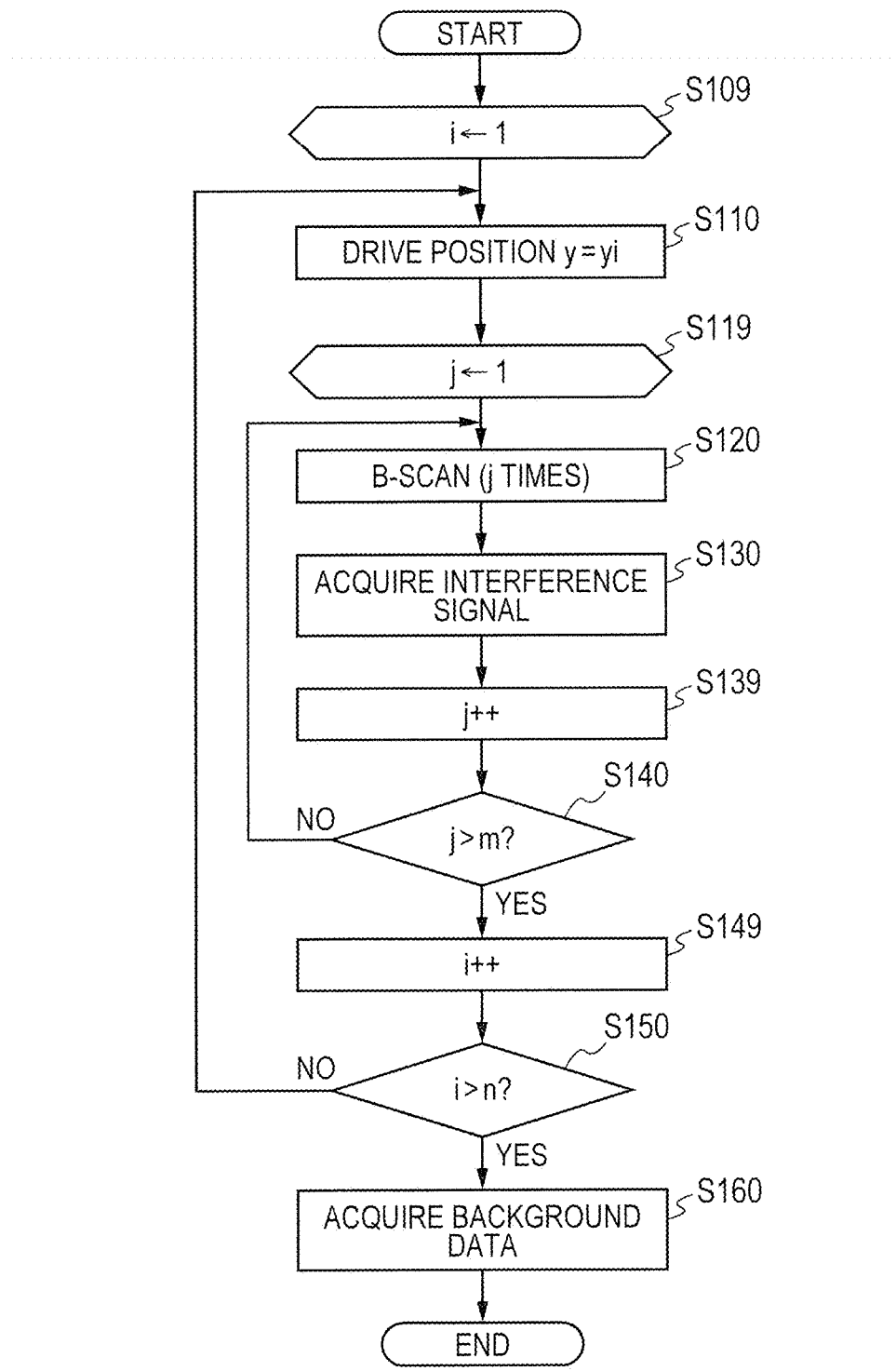
FIG. 4 is a flowchart for illustrating an interference signal acquisition procedure according to the first embodiment.

Next, referring to FIG. 4, a specific processing procedure of Step S101 and Step S102, which are the first signal acquisition step and the second signal acquisition step according to this embodiment, respectively, is described.

In Step S109, the signal acquisition control portion 145 sets an index i of a position yi of FIGS. 2 to 1.

In Step S110, the OCT apparatus 100 drives a scan position to the position yi. In Step S119, the signal acquisition control portion 145 sets an index j of a repetitive B-scan to 1. In Step S120, the OCT apparatus 100 performs the B-scan.

In Step S130, the detector 141 detects the interference signal for each A-scan, and the detected interference signal is stored in the signal processing portion 144 via an A/D converter (not shown). The signal processing portion 144 acquires p samples of the interference signals of the A-scan, to thereby acquire the interference signals corresponding to one B-scan.

In Step S139, the signal acquisition control portion 145 increments the index j of the repetitive B-scan.

In Step S140, the signal acquisition control portion 145 determines whether or not j is larger than a predetermined number of times (m). In other words, the signal acquisition control portion 145 determines whether or not the B-scan at the position yi has been repeated m times. When the B-scan at the position yi has not been repeated m times, the flow returns to Step S120, and the measurement of the B-scan at the same position is repeated. When the B-scan at the position yi has been repeated m times, the flow proceeds to Step S149. In Step S149, the signal acquisition control portion 145 increments the index i of the position yi. In Step S150, the signal acquisition control portion 145 determines whether or not i is larger than a predetermined number of times of y-position measurement (n), that is, determines whether or not the B-scan has been performed at all of the n y-positions. When the measurement has not been performed by the predetermined number of times of y-position measurement (no), the flow returns to Step S110, and the measurement at the next measurement position is repeated. When the measurement has been performed by the predetermined number of times of y-position measurement (yes), the flow proceeds to the next Step S160. In Step S101 and Step S102 described above, which are the first signal acquisition step and the second signal acquisition step, n is set to 1 and m is set to 4.

In Step S160, the OCT apparatus 100 acquires background data. The OCT apparatus 100 executes the A-scan 100 times under a state in which a shutter (not shown) is closed, and the signal acquisition control portion 145 averages signals acquired through one hundred times of the A-scan and stores the resultant signal. The number of times of measurement of the background is not limited to one hundred times as exemplified above.

After the execution of the above-mentioned processing steps, the interference signal acquisition procedure according to this disclosure is brought to an end.

In acquisition of an OCTA interference signal, by setting the number of times of measurement and the position to values suited to the acquisition of the OCTA interference signal, the OCTA interference signal can be acquired with a procedure similar to that of the acquisition of the OCT signal.

In this embodiment, in order to acquire the OCT signals and form the three-dimensional tomographic image, an object-to-be-inspected image to be displayed two-dimensionally is generated based on data acquired from the interference signal set formed of the OCT signals. As described above, the range from which the OCT signal is acquired does not need to be the same as the range from which the OCTA signal is acquired. Thus, as described above, this object-to-be-inspected image is generated as an image within the first area including the second area of the eye to be inspected 118 from which the OCTA signal is acquired.

[Signal Processing Procedure]

Figure 5:
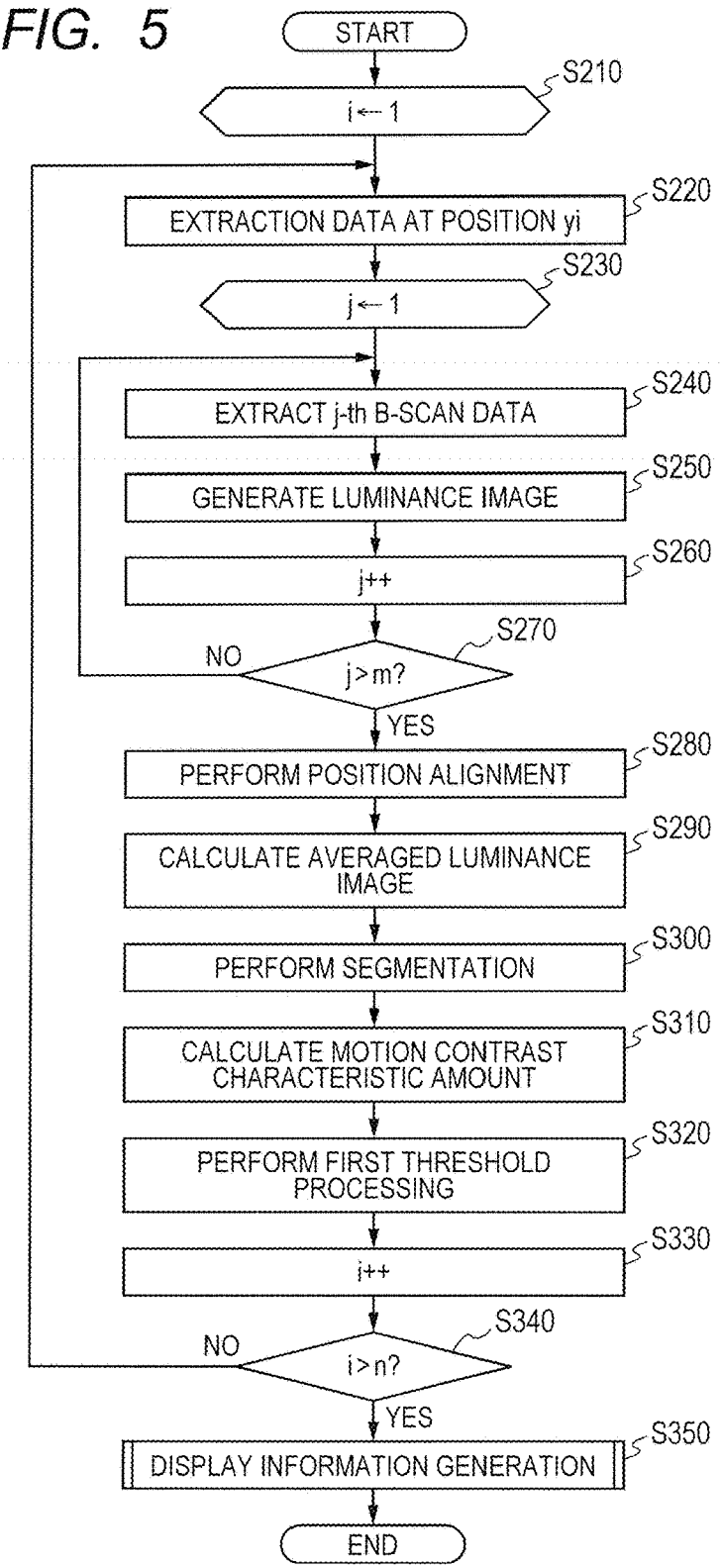
FIG. 5 is a flowchart for illustrating a signal processing procedure according to the first embodiment.

Next, referring to FIG. 5, specific processing of generating display information including three-dimensional image information of OCT and three-dimensional blood flow region information of OCTA, which is performed in Step S103 of FIG. 3 according to this embodiment, is described. In this disclosure, in order to generate the three-dimensional blood flow region information based on the OCTA information, the motion contrast of OCTA is calculated.

In Step S210, the signal processing portion 144 sets the index i of the position yi to 1. In Step S220, the signal processing portion 144 extracts the interference signals of the repetitive B-scan (corresponding to m times of the B-scan) at the position yi (i=1 in this case). In Step S230, the signal processing portion 144 sets the index j of the repetitive B-scan to 1. In Step S240, the signal processing portion 144 extracts j-th (j=1 in this case) B-scan data.

In Step S250, the signal processing portion 144 performs reconstruction processing on the interference signal of the B-scan data extracted in Step S240, to thereby generate a luminance image of the tomographic image. First, the image generation portion 147 removes from the interference signal a fixed pattern noise formed of the background data. The fixed pattern noise is removed by averaging A-scan signals of the detected plurality of pieces of background data to extract a fixed pattern noise and subtracting the fixed pattern noise from the input interference signal. Next, in order to optimize a depth resolution and a dynamic range, which have a trade-off relationship when Fourier transform is performed at a finite interval, the image generation portion 147 performs a desired window function. After that, the image generation portion 147 performs FFT to generate the luminance image of the tomographic image.

In Step S260, the signal processing portion 144 increments the index j of the repetitive B-scan. In Step S270, the signal processing portion 144 determines whether or not the incremented j is larger than m. In other words, the calculation of the luminance of the B-scan at the position yi has been repeated m times. When the determination results in "no", the flow returns to Step S240, and the calculation of the luminance of the repetitive B-scan at the same y-position is repeated. When the determination results in "yes", the flow proceeds to the next step.

In Step S280, the signal processing portion 144 performs the position alignment on m frames of the repetitive B-scan at the given position yi. Specifically, first, the signal processing portion 144 selects from among the m frames an arbitrary one frame as a template. The frame to be selected as the template may be selected by calculating a correlation for every combination of frames, calculating a sum of correlation coefficients for each frame, and selecting one of the frames having the largest sum. Next, the template is compared with each of the frames to calculate a positional deviation amount ($\delta X$, $\delta Y$, $\delta \theta$) of each of the frames. Specifically, a normalized cross-correlation (NCC), which is a mark indicating a similarity, is calculated while changing the position and angle of the template image, and the difference between image positions at the time when the NNC is the largest is acquired as the positional deviation amount.

In this disclosure, the mark indicating the similarity may be changed to various scales as long as the scale indicates a similarity between features of images within the template and the frame. For example, a sum of absolute difference (SAD), a sum of squared difference (SSD), a zero-means normalized cross-correlation (ZNCC), a phase only correlation (POC), or a rotation invariant phase only correlation (RIPOC) may also be used.

Next, the signal processing portion 144 applies position correction to m-1 frames other than the template depending on the positional deviation amount ($\delta X$, $\delta Y$, $\delta \theta$), to thereby perform the position alignment of m frames. Further, when the three-dimensional image information of OCT and the three-dimensional blood flow region information of OCTA are acquired in different steps as in this embodiment, position alignment is also performed between the three-dimensional image information and the three-dimensional blood flow region information. In other words, the position alignment is performed between data of the three-dimensional tomographic image calculated based on the interference signal set acquired for the purpose of generating the OCT intensity image and data of the three-dimensional tomographic image calculated based on the interference signal set acquired for the purpose of generating the motion contrast image. Through execution of the position alignment between those pieces of data, understanding of correspondence between the three-dimensional image information and the three-dimensional blood flow region information can be facilitated. The above-mentioned position alignment may be performed by a method similar to that of the position alignment between the frames.

In Step S290, the signal processing portion 144 averages the luminance image subjected to the position alignment, which is calculated in Step S280, to thereby generate an averaged luminance image.

In Step S300, the map generation portion 148 executes segmentation (region information acquisition) of the retina from the averaged luminance image generated in Step S290 by the signal processing portion 144. In the first embodiment described here, this step is not used, and hence this step is skipped. This step is described in a second embodiment of this disclosure.

In Step S310, the image generation portion 147 calculates a motion contrast. In this embodiment, a variance is calculated for each pixel at the same position from the luminance image of each of the m frames of tomographic images output in Step S250 by the signal processing portion 144, and the calculated variance is determined as the motion contrast.

There are various types of methods of calculating the motion contrast. For example, the type of characteristic amount to be used as the motion contrast in this disclosure is a change in luminance value of each pixel of a plurality of B-scan images at the same y-position. Therefore, any mark that indicates this change in luminance value may be applied to calculate the motion contrast. Further, instead of using the variance for each pixel at the same position, which is acquired from the luminance image of each of the m frames of the tomographic image, the motion contrast may be acquired by another method. For example, a coefficient of variation normalized with an average value of the same pixels of the respective frames may also be used.

In Step S320, the signal processing portion 144 executes first threshold processing on the motion contrast output by the signal processing portion 144. A first threshold value is calculated based on the averaged luminance image output in Step S290 by the signal processing portion 144. Specifically, an area in which only random noise is displayed in a noise floor is extracted from the averaged luminance image to calculate a standard deviation σ, and "(average luminance in noise floor)+2σ" is set as the first threshold value. The signal processing portion 144 sets the value of the motion contrast corresponding to an area in which each luminance is equal to or smaller than the first threshold value to 0.

Through the first threshold processing of Step S320, noise can be reduced by removing the motion contrast originating from a change in luminance due to the random noise.

As the first threshold value becomes smaller, sensitivity of detecting the motion contrast increases, whereas a noise component also increases. In contrast, as the first threshold value becomes larger, noise decreases, whereas the sensitivity of detecting the motion contrast also decreases. In this embodiment, the threshold value is set to "(average luminance in noise floor)+2σ", but the threshold value is not limited thereto.

In Step S330, the signal processing portion 144 increments the index i of the position yi.

In Step S340, the signal processing portion 144 determines whether or not i is larger than n. In other words, the signal processing portion 144 determines whether or not the position alignment, the calculation of the averaged luminance image, the calculation of the motion contrast, and the threshold processing have been performed at all of the n y-positions.

When the determination results in "no", the flow returns to Step S220. When the determination results in "yes", the flow proceeds to the next Step S350.

At the time when Step S340 is finished, three-dimensional motion contrast data (three-dimensional data) on each pixel of the B-scan images (data in Z-axis (depth) and X-axis directions) has been acquired at all of the y-positions. In Step S350, the signal processing portion 144 performs display information generation processing based on those pieces of three-dimensional image information.

Figure 6:
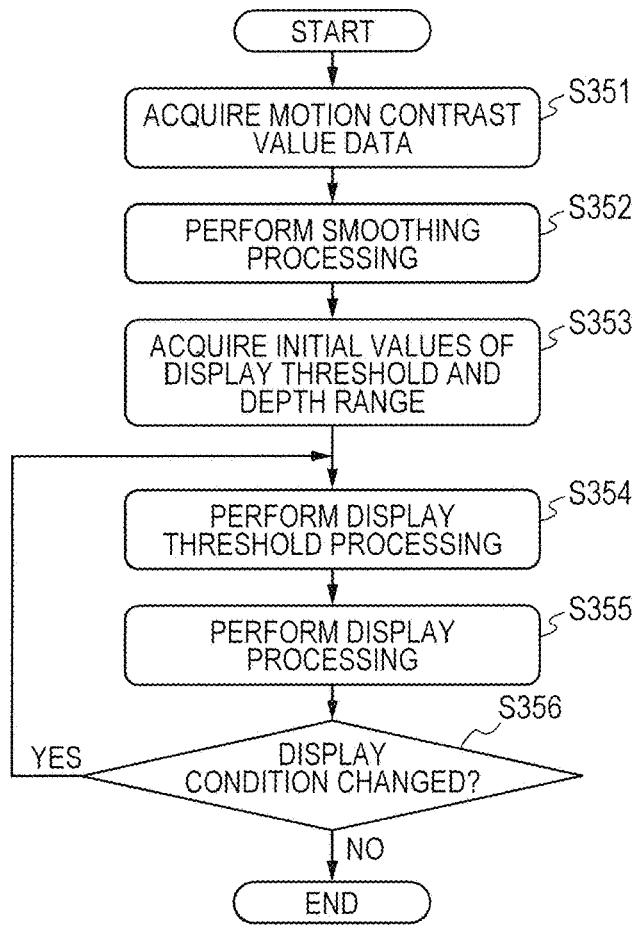
FIG. 6 is a flowchart for illustrating a three-dimensional blood flow region information acquisition and display procedure according to the first embodiment.

Now, the display information generation processing according to this embodiment is described. FIG. 6 is a flowchart for illustrating details of the processing executed in Step S350.

In the generation of the display information, in Step S351, the signal processing portion 144 acquires the three-dimensional motion contrast data acquired in the above-mentioned processing.

In Step S352, in order to remove noise without removing the blood flow region information, the signal processing portion 144 performs smoothing processing on the three-dimensional motion contrast data. Although optimal smoothing processing differs depending on a characteristic of the motion contrast, the following smoothing methods are conceivable, for example:

a smoothing method of outputting a maximum value of the motion contrasts from nx×ny×nz voxels near a pixel of interest;

a smoothing method of outputting an average value of the motion contrasts of the nx×ny×nz voxels near the pixel of interest;

a smoothing method of outputting a median value of the motion contrasts of the nx×ny×nz voxels near the pixel of interest;

a smoothing method of weighting with a weight that is based on a distance with regard to the motion contrasts of the nx×ny×nz voxels near the pixel of interest;

a smoothing method of weighting with a weight that is based on the distance and a weight that is based on the difference in pixel value from the pixel of interest with regard to the motion contrasts of the nx×ny×nz voxels near the pixel of interest; and a smoothing method of outputting a value using a weight that is based on a similarity between a motion contrast pattern of a small area around the pixel of interest and a motion contrast pattern of a small area around a surrounding pixel.

Another method of performing smoothing without removing the blood flow region information may also be used.

After the above-mentioned smoothing processing, in Step S353, the signal processing portion 144 acquires, from the display control portion 149, initial values of a threshold value to be used when a pixel to be displayed is determined in Step S354 and a range of display in the depth direction. The initial value of the display range is normally set to about ¼ in the depth direction, and is set to such a position as to include most of the range of a retinal surface layer. The initial value of the display range in this case is not set to the entire range in the depth direction because a network of main vessels and capillary vessels in a surface layer portion is desired to be displayed first in an easy-to-view manner. In other words, when the surface layer portion including the network of main vessels and capillary vessels and an RPE layer, which does not have vessels and contains a large amount of noise, are displayed simultaneously, such display interferes with identification of the network of main vessels and capillary vessels in the surface layer portion. Regarding the initial value of the display threshold value, it suffices that a representative value is acquired in advance from a healthy eye, or the like, to be set as the initial value. As another example, when imaging is performed repeatedly, the last imaging data may be used. Further, the display threshold value may be adjusted in a processing step described later.

Figure 7A:
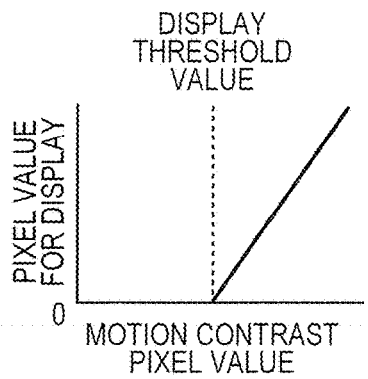
FIG. 7A and FIG. 7B are each an explanatory graph for showing a segmentation result according to the first embodiment.
Figure 7B:
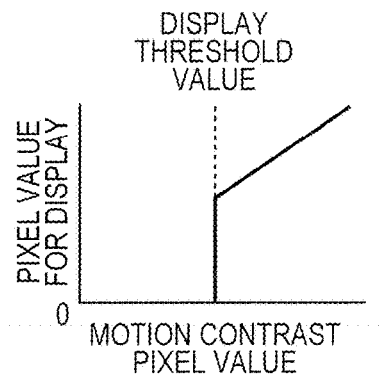

Next, in Step S354, display threshold processing is performed in which the initial value of the display threshold value is used to display a pixel of the three-dimensional data subjected to the smoothing processing that has a pixel value exceeding the initial value. Examples of conversion from a motion contrast into a pixel value for display in this processing are shown in FIG. 7A and FIG. 7B. In FIG. 7A, an example is shown in which a pixel value for display of zero is assigned to a pixel having a motion contrast pixel value equal to or less than the display threshold value and a pixel value for display proportional to the motion contrast pixel value is assigned to a pixel having a motion contrast pixel value of from the threshold value to the maximum intensity. In FIG. 7B, an example is shown in which a pixel value for display multiplied by zero is assigned to a motion contrast pixel value equal to or less than the display threshold value and a pixel value for display multiplied by one is assigned to a motion contrast pixel value greater than the threshold value. In any of the examples, a motion contrast equal to or less than the display threshold value is not used for display, and an area having the motion contrast with the pixel value to be displayed is displayed in a separated manner.

Step S355 illustrated in FIG. 6, which is executed by the display control portion 149, is a step of displaying the motion contrast image subjected to the display threshold processing shown in FIG. 7A and FIG. 7B.

Next, Step S356 is a step of changing a display condition. A display condition that may be changed is described later. When the display condition is changed, the flow returns to Step S354, and an image updated under the changed display condition is displayed. When the display condition is not changed, the display information generation processing is brought to an end.

Next, a display example of an image generated through the display information generation processing according to this embodiment is illustrated in FIG. 8. In the display screen, an intensity image 400, which is the OCT signal displayed as an image, and a motion contrast image 401 are displayed side by side. In this display example, a slider 402 for operating the display threshold value of the motion contrast is provided near the motion contrast image 401.

Further, tomographic images 403 in a part of the intensity image 400 are displayed near the intensity image 400. The tomographic images are displayed in an x-z cross section 403a and a y-z cross section 403b. Further, a line 404 indicating the display position of each tomographic image may be displayed in the intensity image 400 and the motion contrast image 401. The line 404 indicating the display position may be automatically determined based on image information under a specific condition, or may be designated by the inspector. As an example of the specific condition, any condition in which the tomographic image 403 having a macula portion at its center is designated can be used. As another example, the inspector may designate an arbitrary position and length from the intensity image 400 or the motion contrast image 401, and a tomographic image having the designated position and length may be displayed.

Further, a slider 405 may be provided, which is used to designate from each tomographic image a display range of the intensity image 400 or the motion contrast image 401 in the depth direction. In the slider 405, on a bar 405b indicating an adjustable range in the depth direction, a depth at which the intensity image 400 or the motion contrast image 401 is displayed or the display range in the depth direction is designated with a slide portion 405a. Further, a GUI operation portion 406 for operating the display position may be provided. Details of the GUI operation portion 406 are described later. Further, a cursor 407 indicating a selected position may be displayed. In this case, it is preferred that the cursor 407 be displayed as a mark so as to simultaneously indicate corresponding positions of the intensity image 400 and the motion contrast image 401. This display is instructed by the display control portion 149. In the example of FIG. 8, an example in which the intensity image 400 and other images are displayed as two-dimensional planar images is described, but an image to be displayed may also be a three-dimensional image, an arbitrary tomographic image, or a combination thereof.

In other words, in this example, the intensity image 400 that is the first image and the motion contrast image 401 are displayed side by side. Then, in any one of the images, designation of an arbitrary position in the image is received by the cursor 407 located at the designated position, and information on a vessel corresponding to the designated position, which is acquired from the motion contrast image 401, is superimposed onto the intensity image 400 for display.

Further, in this embodiment, the image illustrated in FIG. 8 as a two-dimensional plane is generated based on an OCT intensity signal without using a fundus camera or a scanning laser ophthalmoscope. Such an image is referred to as "enface image". Now, a method of generating the enface image is described briefly.

Pieces of information acquired through the A-scan are arrayed from the light source side in the optical axis direction, and a position at which a strong signal can be acquired first from a position at which there is no signal is information on a fundus surface layer (retinal surface). Therefore, by linking together reflection intensities of the first strong signals of the respective A-scan signals at the measurement positions (imaging positions) on the fundus when the measuring light is scanned along two axes, the enface image of the fundus surface layer for showing the fundus surface layer two-dimensionally can be acquired. Further, in the A-scan signal, several strong signals corresponding to specific layers of the retina are found from the first strong signal. By linking together reflection intensities of strong signals located at a specific order counted from the first strong signal, the enface image at a specific layer or depth of the retina can be acquired. Through the above-mentioned method of acquiring the enface image, the layer structure in the tomographic image of the fundus Er can be detected from data of the three-dimensional tomographic image that is based on the interference signal set.

Further, the tomographic image acquired through the B-scan is constructed by continuously acquiring pieces of information through the A-scan along one-axis direction. Accordingly, through acquisition of corresponding positions of an image signal of a part of the enface image and an image signal of a fundus surface layer portion of the acquired tomographic image, the tomographic image at which position on the enface image the A-scan corresponds to can be detected accurately. When the layer structure is extracted, the display range of the motion contrast image, or the like, may be determined based on the layer structure as described later.

Figure 9:
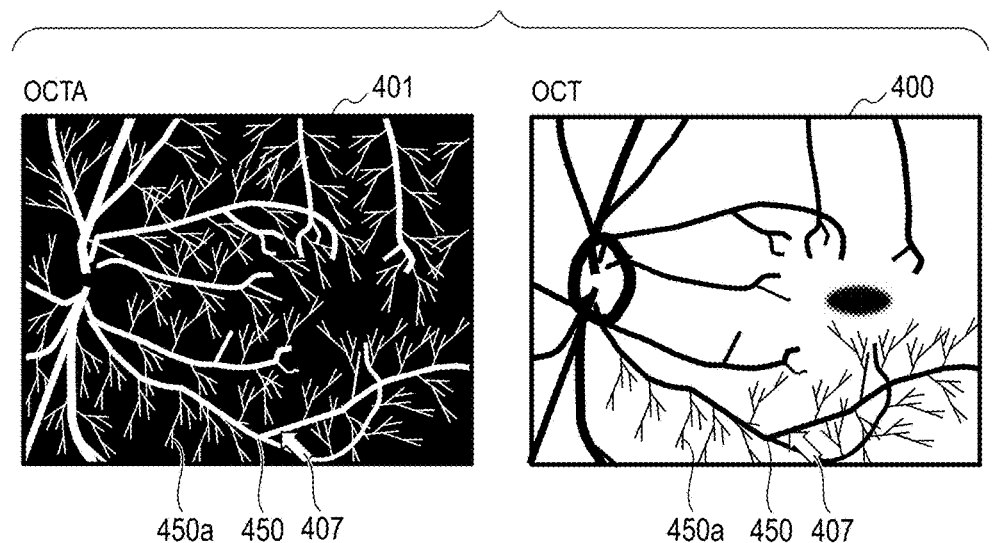
FIG. 9 is a diagram for illustrating an example of a display method according to the first embodiment.

Next, a display operation is described. The display operation is illustrated in FIG. 9. In FIG. 9, the intensity image 400 and the motion contrast image 401 of FIG. 8 are illustrated. As described above, in this embodiment, the OCT interference signal and the OCTA signal are acquired in the same step, and in the generation of the image to be displayed, the position alignment between those signals along the same scan line is finished. Therefore, a correspondence relationship between pixels of the intensity image 400 and the motion contrast image 401 is known in advance.

In the display operation according to this embodiment, when a part of one of the images (e.g., vessel portion of the intensity image) is selected, a corresponding area of the other image (corresponding vessel portion of the motion contrast image) is superimposed onto the original image (intensity image) for display. In an example of FIG. 9, when a vessel portion 450 of the intensity image 400 is selected, a corresponding vessel and vessels 450a connected thereto in the motion contrast image 401 are superimposed onto corresponding positions of the intensity image 400 for display. More specifically, first, a vessel is selected in one of the images. In this case, each pixel or piece of positional information on the vessel is already associated with that of the corresponding other image through the position alignment. Under this state, positional information on the vessel selected in one of the images is acquired. Subsequently, based on the acquired positional information, corresponding positional information in the other image is selected. A vessel in the other image is selected as a corresponding vessel based on the selected positional information. Through the above-mentioned procedure, based on the positional information on the corresponding vessels in the respective images, the vessel of one of the images is superimposed onto the other vessel image for display.

It is assumed that a connection state of vessels (thick vessel and a group of thin vessels branching from the thick vessel) in each of the images is known in advance through area division processing described later.

Therefore, vessels are selected and superimposed in consideration of the connection state (in a manner in which vessel groups are associated with each other). As described later, this superimposition for display is performed by superimposing information (information on the vessel) on one of the intensity image and the motion contrast image, which is selected through input from the cursor 407 or the like, onto an area of the other image in which the information is displayed. This superimposition for display is performed by the display control portion 149 serving as a display control unit, which is configured to display the images superimposed onto each other in the above-mentioned manner on the display portion 146 serving as a display unit.

As a specific method of selecting the image, as illustrated in FIG. 9, a specific vessel may be selected, or an area may be designated. An area to be designated may be a rectangular area, or may be a circle having a fixed distance from the cursor 407. Further, when the size of an OCTA measurement area is smaller than that of an OCT measurement area, the entire motion contrast image may be superimposed. Still further, a display color of a vessel of the other image (motion contrast image) to be superimposed onto the original image may be changed so that which vessel is superimposed onto the original image (intensity image) for display can be viewed.

Although the example in which the motion contrast image is superimposed onto the intensity image is described above, the intensity image may be superimposed onto the motion contrast image. In the case when the intensity image is superimposed onto the motion contrast image, when a specific vessel portion of the motion contrast image 401 is selected, a corresponding vessel and vessels connected thereto in the intensity image 400 are superimposed onto corresponding positions of the motion contrast image 401 for display. In this case, it is preferred that, in order to enhance visibility, a portion corresponding to the vessel portion superimposed for display be expressed by a thick line and a line obtained by superimposing dotted lines onto one another. As another example, a display color of a vessel to be superimposed may be changed. In general, a vessel that can be identified from the intensity image is a relatively thick vessel, and, hence, understanding of correspondence to structural information of the intensity image in terms of positions can be facilitated. Therefore, by superimposing the intensity image onto the motion contrast image in this manner, a thick vessel can be used as a mark, and comparison with structural information other than a vessel can be easily performed. Further, through use of the intensity image 400 as a basis, not only a vessel, but also, other structural information, e.g., a macula or a lesion, can be displayed together.

As described above, with the configuration in which one of the image information of the OCT intensity image and the image information of the OCTA motion contrast image can be superimposed onto the other image information for display, understanding of correspondence between the intensity image and the motion contrast image can be facilitated. Therefore, an image that is easy to understand intuitively can be provided.

As an example of display according to this embodiment, display of a cursor is described. As illustrated in FIG. 8 and FIG. 9, the cursor 407 may be displayed in both of the intensity image 400 and the motion contrast image 401. The shape of the cursor 407 may be, for example, an arrow as illustrated in the figures, or may be a circle or a rectangle. Further, the cursors 407 of the images may have different shapes. As another example, the shape of the cursor 407 may be crosses crossing each other in the X-axis direction and the Y-axis direction. The cursors indicate corresponding positions of both images simultaneously. It is desired that the cursor be freely movable through an operation of a mouse (not shown), or the like, attached to the image forming apparatus. Further, a cut position of the tomographic image may be changed in response to the movement of the cursor. Through simultaneous display of corresponding positions, the images can be easily compared with each other.

Next, as an example of a change in the display condition according to this embodiment, a change of the display range and a viewpoint is described. Display magnifications and display positions of the images or a viewpoint position may be changed simultaneously. For example, the display condition is changed through the GUI operation portion 406 of the display screen of FIG. 8. Through use of a "zoom" button 406a, both images are enlarged (+) or reduced (−) simultaneously. Further, when the images are enlarged, through use of a "move" button 406b, the display ranges of both images are moved in parallel simultaneously. Similarly, through use of a "rotate" button 406c, display viewpoints of both images are rotationally moved simultaneously. The rotational movement can be applied when both images are displayed three-dimensionally. In other words, with this configuration, at least one of the magnifications, the displayed positions, and the viewpoint positions of the intensity image and the motion contrast image can be changed simultaneously in both images.

Although the example in which the GUI operation portion 406 includes three types of buttons is described above, the number of buttons and the shape and type of each button may be different from those of the example. Another method may be used instead. For example, the display range and the viewpoint may be changed through an operation of the mouse attached to the image forming apparatus. The images may be enlarged or reduced by superimposing a cursor of the mouse onto one of the images and operating a wheel of the mouse, and the images may be moved (in parallel or rotationally) by moving the mouse while pressing a button of the mouse. As an example other than the mouse, in the case of the touch panel, the image displayed on the panel may be operated by a finger. In any case, it suffices that the display ranges and the viewpoints of the intensity image and the motion contrast image displayed side by side can be changed simultaneously. With this configuration, how the image is displayed is changed simultaneously in both of the intensity image and the motion contrast image, and hence, even when how the image is displayed is changed, a specific position being viewed can be easily understood.

The display threshold value of the motion contrast pixel value is described. In FIG. 8, the slider 402 for adjusting the threshold value of the pixel to be displayed is provided. An initial position of the display threshold value may be a representative value set in advance. When the inspector drags the slider with the mouse, the signal processing portion 144 determines in Step S356 of FIG. 6 that the display condition is changed (YES). The signal processing portion 144 changes the display threshold value, and returns the processing to Step S354 to update the three-dimensional motion contrast image to be displayed. At this time, when setting is made so that the threshold can be adjusted with a relative value with respect to the initial value, an equivalent effect can be obtained even for data of a different object, e.g., a different eye to be inspected or region.

Next, a modified example of the method of displaying vessel information is described. In this case, a step of acquiring vessel information from a two-dimensional motion contrast image is performed. The step of acquiring the vessel information may be performed simultaneously with Step S352, which is the smoothing processing step, or may be performed after Step S352. Specifically, a step of applying the smoothing processing data and a step of performing processing of dividing an area corresponding to a vessel are performed on the motion contrast data. Through execution of those steps of processing, a smooth vessel area can be extracted.

Figure 13:
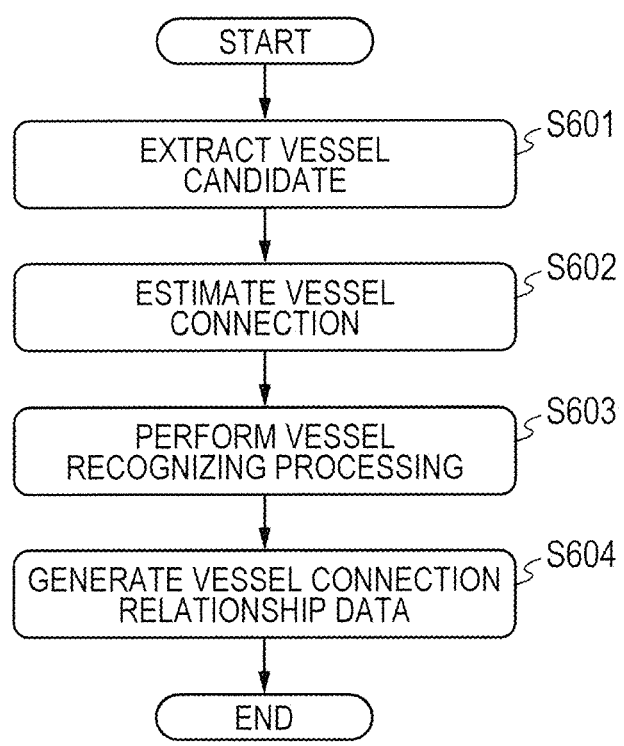
FIG. 13 is a flowchart for illustrating an example of an area division processing procedure.

Next, the area division processing is described. An example of a flow of the area division processing is illustrated in FIG. 13.

First, in Step S601, which is a vessel candidate extraction step, the signal processing portion 144 executes processing of extracting a pixel having a pixel value representing the volume data corresponding to the motion contrast of the pixel of interest that is equal to or greater than a predetermined threshold value as a vessel candidate.

Next, in Step S602, which is a vessel connection estimation step, the signal processing portion 144 executes processing of estimating, for each of the extracted pixels that are the vessel candidates, whether or not there is a vessel connection relationship, which is a connection relationship between those vessels. In the vessel connection estimation step, for each of the pixels that are the vessel candidates, when an adjacent pixel has a pixel value equal to or greater than the predetermined threshold value, or when the adjacent pixel is also extracted in advance as the vessel candidate, it is determined that those pixels are connected vessel candidates. When a specific pixel is determined to be a connected vessel candidate in this manner, the range of estimation is expanded to a further adjacent pixel. When the pixel value of the adjacent pixel is less than the threshold value (or when the adjacent pixel is not the vessel candidate),the adjacent pixel is excluded from the vessel candidate, and another adjacent pixel is estimated. It suffices that the operation of vessel connection estimation is performed on all or a designated range of the vessel candidates.

After the estimation of all adjacent pixels of the vessel candidate or all pixels is completed, the signal processing portion 144 performs processing of Step S603, which is a vessel recognizing processing step, based on the size of the connected vessel candidate. In the vessel recognizing processing, the vessel candidate having a predetermined number or more of pixel connections is identified as the same relatively thick or main vessel.

Finally, in Step S604, which is a vessel connection relationship data generating step, the signal processing portion 144 executes processing of generating first vessel connection relationship data. The first vessel connection relationship data contains at least information on a three-dimensional distribution of connected vessels and information on the connection of vessels. For example, volume data containing information for identifying, for each pixel, whether or not a vessel exists and identifying each vessel may be used as the first vessel connection relationship data.

The above-mentioned threshold value for extracting the vessel candidate may be a value determined in advance, or may be changeable. For example, the OCTA signal of the eye to be inspected is measured, and the inspector may adjust the threshold value after seeing how areas are divided as vessels. As another example, a representative value may be set as an initial value of the threshold value. When the motion contrast data is binarized into a vessel area and another area in the area division step, the vessel candidate may be extracted through use of a result of binarization. Similarly, the threshold value of the predetermined number of connections, which is used for the determination of a pixel as a vessel, may be a value determined in advance, or may be changeable. For example, when a plurality of pixels are connected, those pixels may be determined to be the vessel candidate, and when there is only a single pixel, the pixel may be excluded from being the candidate. Through execution of such processing, an isolated area can be excluded from the motion contrast image, and connected vessels can be extracted. Examples of the isolated area include a local and random change in reflection intensity, e.g., a speckle noise.

Figure 14A:
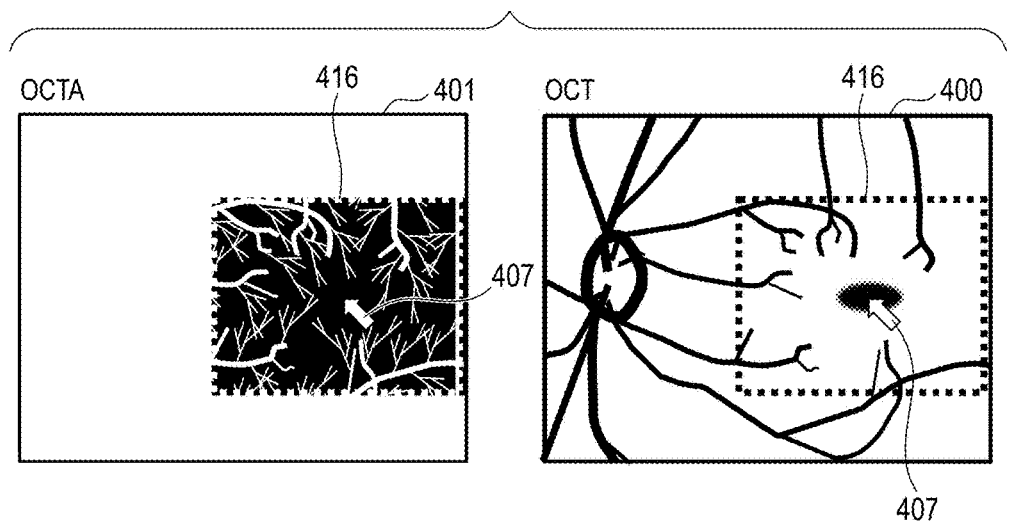
FIG. 14A and FIG. 14B are each a diagram for illustrating an example of a display method of displaying two images.
Figure 14B:
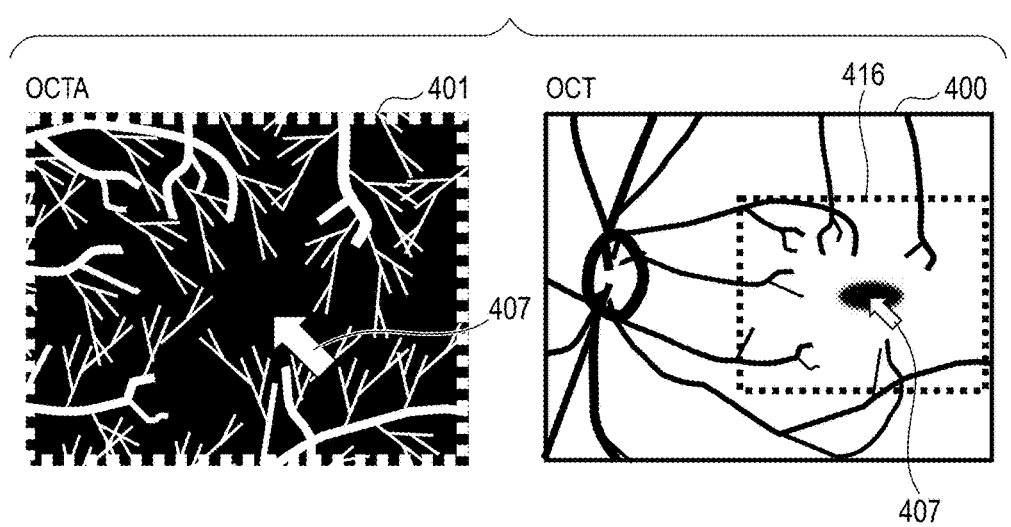

Further, although the example in which the intensity image and the motion contrast image have the same size is described, as described above, even when the size of a range in which the motion contrast image is acquired is small, those images can be displayed similarly. An example in which the intensity image and the motion contrast image have different sizes is illustrated in FIG. 14A and FIG. 14B. FIG. 14A is an illustration of an example in which the size of the motion contrast image is changed such that scales of the images match. FIG. 14B is an illustration of an example in which the scale of the motion contrast image is changed such that the sizes of the images match. In this case, it is preferred that, in one of the images having a wider angle of view, a frame line 416 indicating a display area of the other image be displayed. Further, the zoom button 406a and other buttons illustrated in FIG. 8 may be used to enlarge or reduce the intensity image and the motion contrast image, move the viewpoints of the images, or superimpose the state of one of the images onto the other image.

Figure 15:
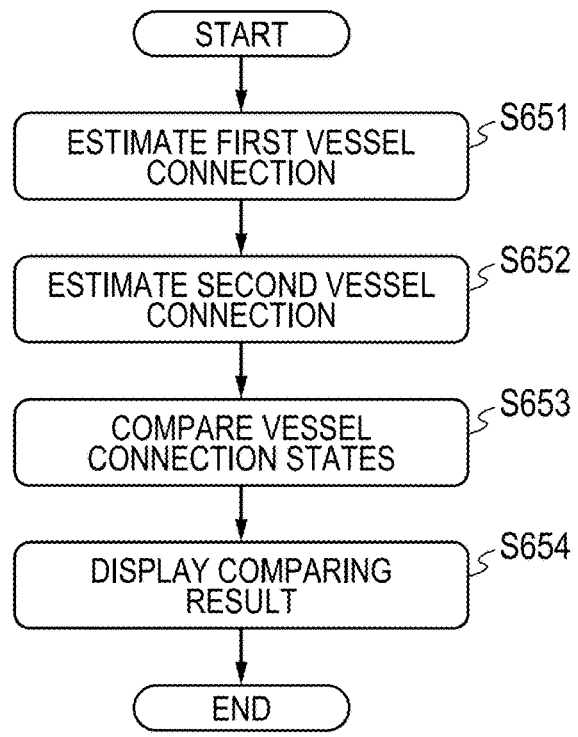
FIG. 15 is a flowchart for illustrating an example of a comparison procedure to be performed when a vessel is estimated.

Next, an example in which a vessel acquired from the intensity image and a vessel acquired from the motion contrast image are compared with each other is described. An operation performed in this case is described with reference to a flowchart of FIG. 15.

First, in Step S651, which is a first vessel connection estimation step, the signal processing portion 144 executes processing of estimating a first vessel connection relationship from a two-dimensional motion contrast image. In Step S651, the first vessel connection relationship can be estimated by a method similar to the method used in Step S602 described above to estimate the connection relationship of the vessels.

Next, in Step S652, which is a second vessel connection estimation step, the signal processing portion 144 executes processing of estimating a second vessel connection relationship from three-dimensional tomographic image data. It suffices that the second vessel connection relationship is estimated for a specific layer. For example, it suffices that, of the three-dimensional tomographic image data, the three-dimensional tomographic image data having a depth corresponding to the retinal layer is used to generate a two-dimensional intensity image (e.g., intensity image 400) to further estimate the second vessel connection relationship. In the intensity image, the intensity of a signal acquired from a vessel is relatively weaker than that of a surrounding area due to, for example, absorption by blood, or the like. In this case, through selection of the retinal layer, a pixel corresponding to a retinal arterial and venous vessel can be easily extracted as a vessel.

It suffices that division of an area corresponding to a vessel is performed by a method similar to that of the motion contrast data. Further, it suffices that a value corresponding to the intensity image is set as the threshold value of a pixel to be used when the pixel is extracted as a vessel. A vessel acquired through the estimation of the second vessel connection relationship is information originating from vascular structure, although its resolution with which a vessel can be extracted is lower than that of the connection relationship of vessels (first vessel connection relationship) acquired from the motion contrast data.

Next, in Step S653, which is a vessel connection state comparing step, the signal processing portion 144 executes processing of comparing connection states of vessels having the second vessel connection relationship and the first vessel connection relationship. It suffices that the comparison between the connection states of vessels is performed by comparing corresponding positions of the first and second vessel connection relationships as to whether or not there is a vessel.

Next, in Step S654, which is a comparing result display step (display step), the control portion 143 superimposes, for display on the display portion 146, at least a part of a result of the comparison between the connection states of vessels onto the intensity image and/or the motion contrast image. For example, a portion that is not estimated as a vessel in the other image is displayed. Instead, a portion that is estimated as a vessel in both images may be displayed. An area to be subjected to the comparison may be the entire image, or may be only a specific area.

Superimposition of the vessel image of the motion contrast image onto the intensity image corresponds to superimposition of information on capillary vessels that cannot be acquired from the intensity image onto the intensity image for display. In contrast, superimposition of the vessel image of the intensity image onto the motion contrast image corresponds to display of an area in which a blood flow stagnates. In the area in which the blood flow stagnates, a motion contrast pixel value is less than that of an area in which the blood flows smoothly. When the pixel value is equal to or less than a threshold value, it is determined that there is no vessel. Examples of the area in which the blood flow stagnates include a portion in which stagnation occurs due to an aneurysm, a region in which a region having a small internal diameter exists in the middle of a path, and an area in which the vessel is occluded.

Through the above-mentioned superimposition of information on the connection state of vessels of one of the images onto the other image, those images can be compared with each other even more easily.

Moreover, in the display of a vessel, a specific vessel may be selected to be highlighted. In this case, after Step S654, which is the comparing result display step, a step of selecting a pixel near a specific vessel is further provided. Specifically, for example, an arbitrary pixel is selected from a displayed image with the mouse, or the like. In response to this selection operation, the signal processing portion 144 selects a vessel immediately near the selected pixel. In this case, the selected vessel has the above-mentioned information on the first and second vessel connection relationships. For the selected vessel, a result of comparing vessels acquired from the intensity image and the motion contrast image with each other is displayed. It suffices that the result of comparison is displayed by, for example, superimposing a translucent vessel image having a different color for display. An example in which a specific vessel is selected and the vessel image of the motion contrast image is superimposed onto the intensity image is illustrated in FIG. 9.

An aspect having a plurality of modes as a mode of selecting a vessel for superimposition is conceivable. As the mode in this case, for example, a mode of superimposing a portion of a vessel designated by the cursor 407 from a papilla to an end portion onto the intensity image 400 is conceivable. Further, the plurality of modes may include a mode of superimposing a portion of a vessel designated by the cursor 407 from a designated position to the end portion onto the intensity image. Further, the plurality of modes may include a mode of designating an area with the cursor 407 and superimposing a vessel included in the designated area onto the intensity image 400. Further, the plurality of modes may include a mode of executing estimation of a vascular diameter described later and, at the time of superimposition, not superimposing a vessel whose diameter is estimated to be equal to or less than a predetermined vascular diameter. Further, those modes may be combined with each other.

With this configuration, a comparison result focusing on a specific vessel can be acquired. For example, one of the retinal arterial and venous vessels may be selected, and a state of a vessel connected to the selected vessel may be extracted for display. As another example, instead of selecting a specific vessel, the image may be separated into different colors in advance for each extension of a vessel from an optic nerve head. For example, the image may be separated into different colors on the basis of directions in which vessels spread from the center of the optic nerve head.

A step of acquiring the vessel information from the vessel extracted from the motion contrast image may be further provided. For example, at least a vascular diameter of a vessel area may be detected. The vascular diameter is obtained by approximating the extracted vessel by a cylinder and estimating an axial direction and a radial direction of the cylinder. Data of the vascular diameter may be further added to, for example, the volume data of the first vessel connection relationship data (information on a three-dimensional distribution of vessels and information on the connection of vessels). With this configuration, information on the form of vessels can be acquired from the motion contrast image.

Figure 16:
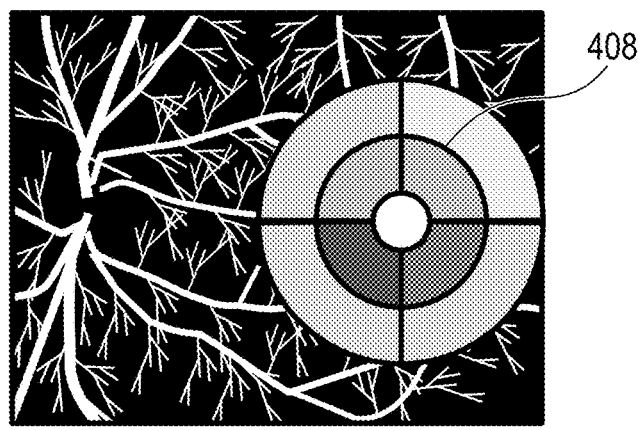
FIG. 16 is a diagram for illustrating an example of a method of displaying an analysis result of the vessel estimation.

Further, vessels may be classified based on the calculated vascular diameter. First, a thin vessel having a diameter smaller than a predetermined diameter is extracted. It suffices that, for example, a diameter of a capillary vessel is set as the predetermined diameter. Then, in a predetermined area of the motion contrast image, a presence ratio between pixels extracted as the thin vessel (e.g., capillary vessels) and other pixels is calculated. Further, the presence ratio is mapped two-dimensionally for display. With this configuration of mapping, a density of vessels can be visualized quantitatively. It suffices that the predetermined area is divided into areas on the basis of, for example, the macula (or optic nerve head). FIG. 16 is an illustration of an example of mapping. In the example of FIG. 16, a map 408 in which a given area is divided into a plurality of areas around a macula portion is superimposed onto a two-dimensional motion contrast image. Through division into the plurality of areas, a qualitative evaluation of the density of capillary vessels can be easily performed. Further, mapped information may be superimposed for display not only onto the motion contrast image but also onto the two-dimensional intensity image, or may be displayed on another screen.

With this configuration, information on the form of vessels can be visualized in association with the intensity image from the motion contrast image.

(Second Embodiment)

Next, as the second embodiment, a change of the display range in the depth direction is described.

Through an operation of the slider 405 of FIG. 8, the display ranges to be displayed in the depth direction of the intensity image and the motion contrast image are changed. The slider 405 includes, as described above, the slide portion 405a indicating the depth range to be displayed and the bar 405b indicating the adjustable range of the retina in the depth direction. The slide portion 405a enables a change in the depth direction of a width and position to be displayed as an image, and is used for selecting the display range in the depth direction. In response to the change of the display range through an operation of the slide portion 405a, the intensity image 400 and the motion contrast image 401 to be displayed are updated simultaneously. With the configuration according to this embodiment, the display ranges in the depth direction are changed simultaneously, and hence even when the range of the displayed depth of an image is changed, a specific position being viewed can be easily understood.

Although the example in which the slider is used is described above as a method of changing the depth range, another method may be used. For example, a method of substantially changing the displayed depth by displaying the image for each layer of the layer structure of the eye to be inspected may be used. This embodiment includes a step of detecting, from the three-dimensional tomographic image data, layers of the layer structure of the tomographic image of the eye to be inspected (corresponding to Step S300 of FIG. 5). In a step of setting the displayed depth, the displayed depth may be selected based on the layer structure information on the eye to be inspected instead of the slider. The layer structure of a human eye is known, and includes the following six layers, for example. The six layers are (1) a nerve fiber layer (NFL), (2) a layer that is a combination of a ganglion cell layer (GCL) and an inner plexiform layer (IPL), (3) a layer that is a combination of an inner nuclear layer (INL) and an outer plexiform layer (OPL), (4) a layer that is a combination of an outer nuclear layer (ONL) and an external limiting membrane (ELM), (5) a layer that is a combination of an ellipsoid zone (EZ), an interdigitation zone (IZ), and a retinal pigment epithelium (RPE), and (6) a choroid.

Segmentation of those layers of the retina is described. The map generation portion 148 applies a median filter and a Sobel filter to a tomographic image to be processed, which is extracted from the intensity image, to generate images (hereinafter referred to also as "median image" and "Sobel image", respectively). Next, a profile is generated for each A-scan from the generated median image and Sobel image. A profile of the luminance value is generated from the median image, and a profile of a luminance gradient is generated from the Sobel image. Then, a peak within the profile generated from the Sobel image is detected. The profile of the median image corresponding to a portion around the detected peak and a portion between the peaks is referred to, to thereby extract a border between areas of the retinal layer. The pixel and the layer are associated with each other based on the extracted border information.

Figure 10:
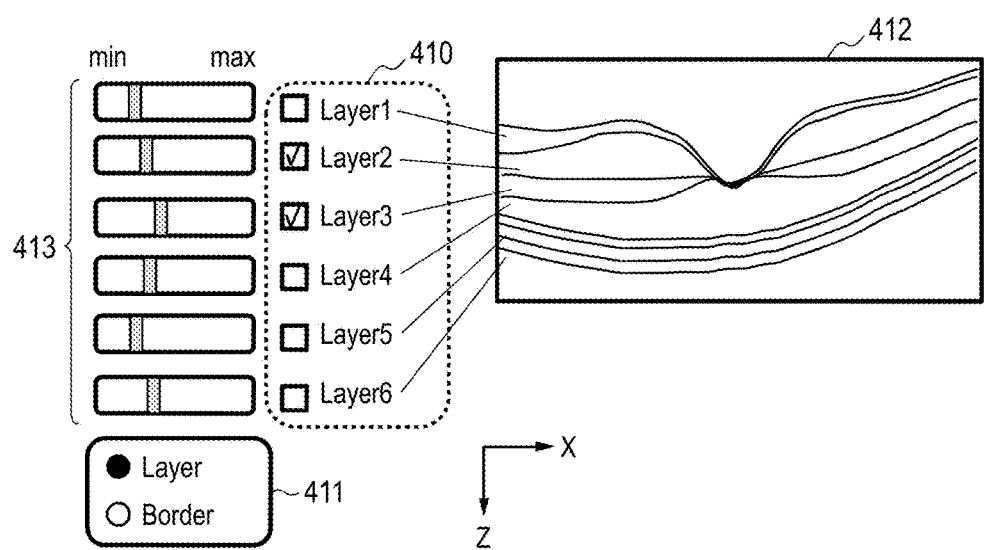
FIG. 10 is a diagram for illustrating an example of a depth selection method according to a second embodiment of this disclosure.

FIG. 10 is an illustration of an example of a method of selecting a layer to be displayed after the segmentation. In this example, selection buttons 410 corresponding to the respective layers in the tomographic image are provided. Through selection of the selection buttons 410, the display range of the image or the layer to be displayed is designated selectively. One selection button 410 may be provided for each layer as illustrated in FIG. 10, or may be provided for each combination of a plurality of layers. For example, a selection button may be provided for each of upper layers and lower layers of the retina. As another example, buttons may be provided so that the display range can be selected on a border-by-border basis. Further, those configurations may be combined. Specifically, radio buttons 411 for switching whether the display range is selected on a layer-by-layer basis or on a border-by-border basis may be provided as illustrated in FIG. 10. Still further, in order to facilitate understanding of correspondence between the buttons and the layers or borders, the tomographic image 412 and the selection buttons 410 and other buttons may be displayed side by side.

In response to the processing of selecting a layer to be displayed, the intensity image and the motion contrast image are updated. A slider 413 for adjusting the display threshold value of the motion contrast image may be provided for each layer so that the display threshold value can be readjusted when the images are updated. With the above-mentioned configuration, the layer to be displayed is changed simultaneously for the intensity image and the motion contrast image, and hence, even when the layer to be displayed is changed, a specific layer being viewed can be easily understood. Further, through a change of the depth range based on the layer structure, information focusing on a specific layer can be displayed.

When the images are displayed based on the layer structure of the eye to be inspected, the intensity image and the motion contrast image may be two-dimensional images. Now, a step of generating the two-dimensional image is described. In the step of generating the two-dimensional image, based on the designated depth or the selected layer, pieces of three-dimensional tomographic image data are projected and integrated in the depth direction within the corresponding range to generate a two-dimensional intensity image. An example of a projection method is described with reference to FIG. 11A and FIG. 11B.

Figure 11A:
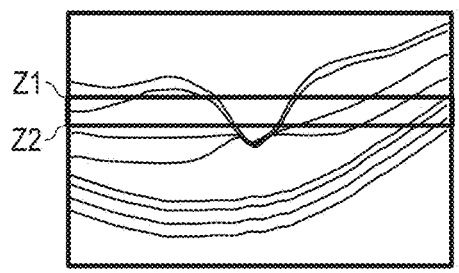
FIG. 11A and FIG. 11B are each an explanatory diagram for illustrating an example of a method of generating a two-dimensional intensity image according to the second embodiment.
Figure 11B:
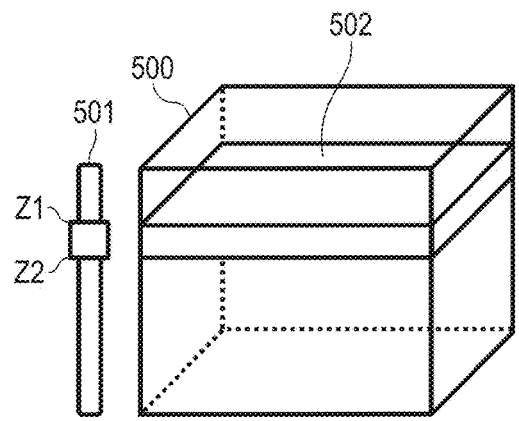

FIG. 11A is an illustration of a tomographic image, and a range between depths Z1 and Z2 in the depth directions corresponds to a selected range. FIG. 11B is an illustration of three-dimensional volume data 500 and a depth indication bar 501. A volume area 502 designated as a range between the depths Z1 and Z2 on the depth indication bar 501 is the selected range. A two-dimensional intensity image can be generated by projecting and integrating voxels within the volume area 502 (the volume data of the three-dimensional tomographic image) in the depth direction. A three-dimensional motion contrast is similarly processed. Specifically, the voxels within the same area are projected and integrated, or projected or integrated, in the depth direction, to thereby generate a two-dimensional motion contrast image.

In other words, in the embodiment described here, the first image is generated by projecting and integrating pieces of three-dimensional tomographic image data of the fundus Er within the display range, and the two-dimensional motion contrast image is generated by projecting and integrating pieces of volume data of the motion contrast image within the display range in the depth direction. It is preferred that those generated images be displayed side by side. Further, at the time of image generation for display, it is preferred that, in order to generate any one of the first image and the two-dimensional motion contrast image, the tomographic image at the position corresponding to the designated position be generated for display based on at least any one of data of the three-dimensional tomographic image and the volume data of the motion contrast image.

The two-dimensional image can be generated not only by integrating the pixel values of corresponding pixels but also by extracting and projecting representative values, e.g., maximum values. The generated two-dimensional images are displayed as the intensity image and the motion contrast image. Further, instead of performing the processes of displaying those images simultaneously, those processes may be performed sequentially such that the display threshold value of the motion contrast image is changed after the two-dimensional motion contrast image is generated and a display state of the image is examined. By generating two-dimensional images and displaying the images side by side, all of the information focusing on a specific layer can be understood at once.

Although the voxels are projected and integrated within the designated fixed depth range in the example illustrated in FIG. 11A and FIG. 11B, the voxels may be projected and integrated within a depth range corresponding to the layer structure. In other words, a depth range corresponding to the layer selected for each position may be selected, and the voxels may be projected and integrated within the selected range. With this configuration, the two-dimensional image further reflecting the layer structure can be generated.

Further, when the above-mentioned two-dimensional image is displayed, the tomographic image may also be displayed side by side as in FIG. 8. In this case, the position of the cross section of the tomographic image is designated on any one of a two-dimensional intensity image and a two-dimensional motion contrast image. Further, as the tomographic image to be displayed, a tomographic image at a position designated from the three-dimensional tomographic image data and/or the three-dimensional motion contrast or at a corresponding position is selected (or generated). The original image from which the position of the tomographic image to be displayed is designated and the tomographic image to be displayed may be combined with each other as necessary. Further, the tomographic image of the motion contrast image may be superimposed onto the tomographic image of the intensity image for display. Still further, the indication line 404 indicating the cross section of the tomographic image may be displayed in both images as illustrated in FIG. 8. With the configuration in which the position of the tomographic image can be designated for display from the two-dimensional image of any one of the intensity image and the motion contrast image, the tomographic image at a position desired to be viewed can be easily displayed.

Figure 12:
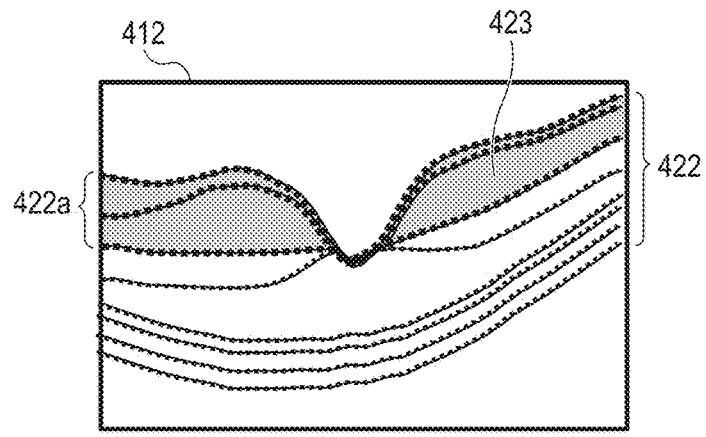
FIG. 12 is a diagram for illustrating an example of a method of displaying a selected region according to the second embodiment.

Further, information on the layer structure may also be displayed in the above-mentioned tomographic image. In this case, based on information obtained by detecting the layer structure of the tomographic image of the eye to be inspected from the three-dimensional tomographic image data, the layer structure is superimposed onto the tomographic image for display. The information on the layer structure may be displayed in any manner as long as each layer of the layer structure can be identified. For example, a line may be displayed on each layer border, or respective layers may be displayed in different colors. An example in which the tomographic image is displayed through division into layers is illustrated in FIG. 12. In the example of FIG. 12, border lines 422 (dotted lines) based on the detected layers are superimposed onto the tomographic image for display. Border lines 422a of selected layers are displayed as thick dotted lines, and a selected layer area 423 is displayed in gray. Through superimposition of the detected information on the layer structure, more understandable display can be achieved.

(Third Embodiment)

Next, a third embodiment of this disclosure is described. In this embodiment, a fundus image is acquired separately from acquisition of the motion contrast image through OCT. The fundus image may be acquired with a fundus camera, a scanning laser ophthalmoscope (SLO), or a vessel image acquired through fluorescence angiography. This configuration forms, as in the configuration for generating the intensity image through OCT according to the first embodiment, an object-to-be-inspected image acquiring unit configured to acquire an object-to-be-inspected image within a first predetermined range of the eye to be inspected 118. As in the intensity image acquired through OCT, a third vessel connection relationship is also calculated from the fundus image acquired through this configuration. The position alignment is performed based on the characteristic amounts of vessels between the calculated vessel connection relationship and the first vessel connection relationship acquired from the motion contrast image. A known position alignment algorithm can be used for the position alignment.

Figure 17:
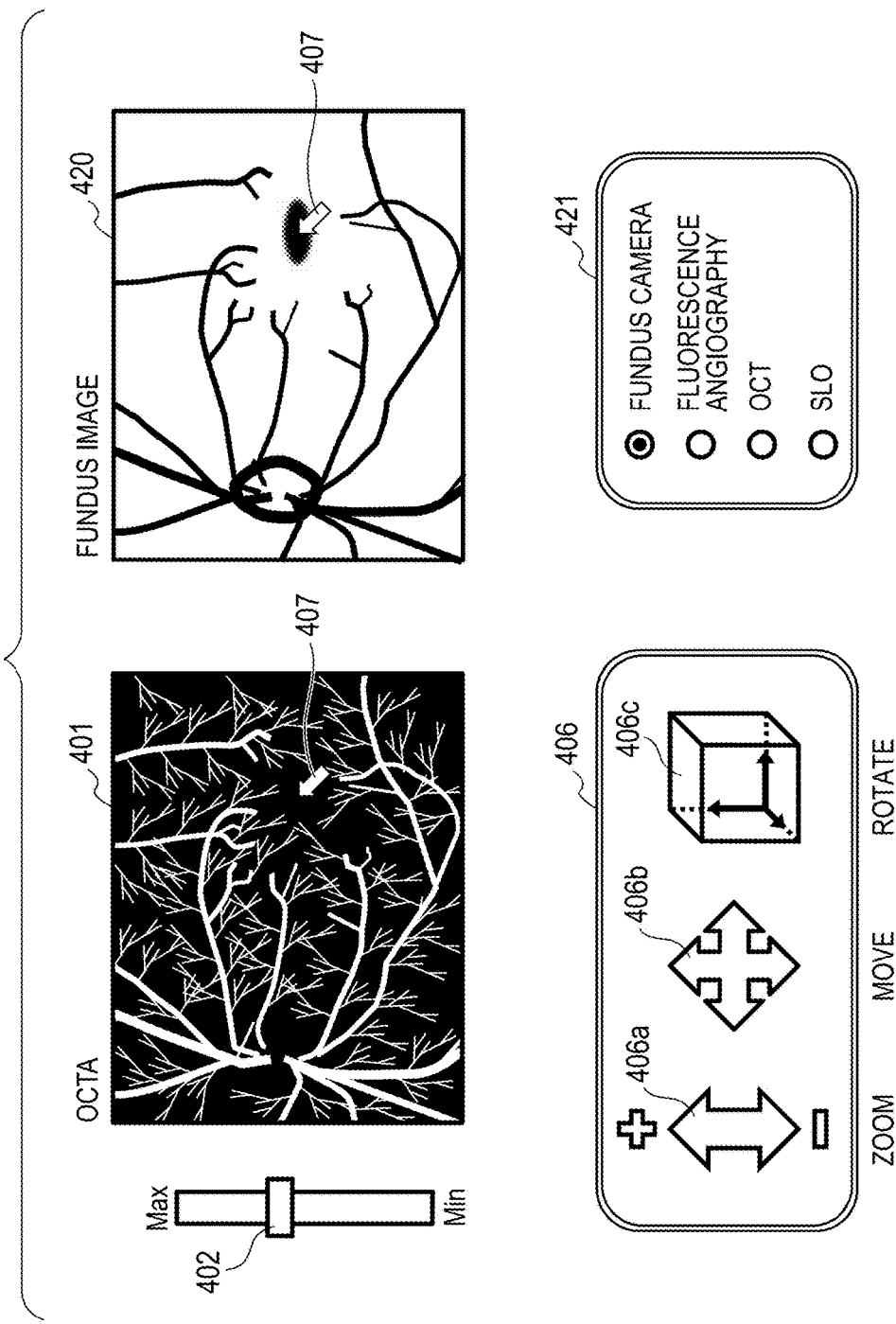
FIG. 17 is a diagram for illustrating an example of a display screen according to a third embodiment of this disclosure.

After the position alignment is performed, the images are displayed side by side. A display example is illustrated in FIG. 17. In the example of FIG. 17, a motion contrast image (OCTA image) 401 and a fundus image 420 are displayed side by side. The fundus image to be displayed is switched through use of a radio switch portion 421. For example, through the switching operation, the fundus image to be displayed is switched among a two-dimensional intensity image acquired through integration of OCT data, the fundus image taken by the fundus camera, and the fundus image taken by the SLO. As in the first embodiment, the cursors 407 are displayed in both images at corresponding positions.

Further, it suffices that both images can be enlarged or moved simultaneously as in the first embodiment (display example illustrated in FIG. 8). With this configuration, an image acquired through another observation apparatus can be easily compared with the motion contrast image. For example, when the motion contrast image and an image acquired from a color fundus camera are displayed side by side, a color vessel photograph and the motion contrast image can be easily compared with each other.

(Fourth Embodiment)

Next, a fourth embodiment of this disclosure is described. In this embodiment, the connection relationship of vessels acquired from the measured motion contrast image and the connection relationship of vessels acquired from another motion contrast image are displayed side by side. It suffices that an image taken previously is used as another motion contrast image. A display example according to the fourth embodiment is illustrated in FIG. 18A and FIG. 18B. In the example of FIG. 18A and FIG. 18B, the motion contrast image 401 on the left side is compared with a motion contrast image 430 on the right side, which was taken in the past. As in the third embodiment, the position alignment is performed between those images based on the connection relationships of vessels. Further, it suffices that both images can be enlarged or moved simultaneously. In this case, the operation executed in the step of acquiring the object-to-be-inspected image in the above-mentioned embodiments is replaced by a step of acquiring another motion contrast image at a time different from the time of the signal acquisition step when the motion contrast image is measured.

In the example of FIG. 18A, an image acquired when a signal of a vessel in an area 431 of the motion contrast image 401 surrounded by the broken lines disappears is illustrated as a schematic diagram. Displayed connection states of both images are compared with each other, and at least a part of a comparison result is superimposed onto any one of the images for display. In FIG. 18B, an example in which a comparison result of the area 431 (vessels) is superimposed for display by the dotted lines is shown. With this configuration, a change with time of the connection relationship of vessels can be easily understood.

The comparison processing executed in this case may be a comparison between a pair of images, or may be a comparison among a plurality of images. When a plurality of images are compared with one another, those images may be displayed in different colors. As another example, an image to be compared may be switched sequentially.

As described above, according to each of the above-mentioned embodiments, information obtained from one of the motion contrast image acquired through OCTA and the intensity image acquired through OCT is displayed in the other image, to thereby enable provision of an image that is easy to understand intuitively. In other words, understanding of correspondence between the motion contrast image acquired through OCTA and the intensity image acquired through OCT can be facilitated. Further, when the images are displayed side by side, images that are easier to be compared with each other can be provided by displaying the cursor indicating corresponding pixels.

Further, through provision of the step in which the magnifications, display positions, and viewpoint positions of both images can be changed simultaneously, even when how the image is displayed is changed, an image enabling easy understanding of a specific position being viewed can be provided.

In the above, the preferred embodiments of this disclosure are described in detail, but this disclosure is not limited to the above-mentioned specific embodiments, and various modifications and changes may be made within the gist of this disclosure described in the appended claims. For example, the positional relationship of the displayed images and the shape of the GUI may be changed. Further, the images may be displayed through stereoscopic vision with a 3D display.

(Other Embodiments)

This disclosure is not limited to the above-mentioned embodiments, and may be carried out with various modifications and changes without departing from the spirit of this disclosure. For example, in the embodiments, a case in which the object to be inspected is an eye is described, but this disclosure is also applicable to an object to be inspected other than an eye, e.g., skin or an organ. In this case, this disclosure includes an aspect as an image forming method or apparatus for forming an image based on data acquired from a medical device other than an ophthalmologic apparatus, e.g., an endoscope. Further, it is desired that the above-mentioned OCT apparatus be understood as an inspection apparatus exemplified by the ophthalmologic apparatus and that the eye to be inspected be understood as one aspect of the object to be inspected.

Embodiment(s) of the present invention can also be realized by a computer of a system or an apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., an application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-009544, filed Jan. 21, 2016, which is hereby incorporated by reference herein in its entirety.

What is claimed is:

1. An image display method comprising:
acquiring a first image of a fundus within a first area of an eye to be inspected;
acquiring interference signal sets corresponding to a plurality of frames, which are acquired with an intention to acquire the same cross section, for a plurality of different cross sections;
generating, based on the interference signal sets corresponding to the plurality of frames, a motion contrast image of the fundus within a second area included in the first area; and
superimposing, for display, information acquired from a portion of the motion contrast image of the fundus onto a corresponding position of the first image of the fundus.

2. An image display method according to claim 1, wherein information on a vessel of the eye to be inspected, which is acquired from a portion of the motion contrast image, is superimposed onto a corresponding position of the first image for display.

3. An image display method according to claim 2, wherein the information on the vessel of the eye to be inspected comprises information indicating a connection state of the vessel.

4. An image display method according to claim 1, further comprising displaying the first image and the motion contrast image side by side.

5. An image display method according to claim 4, further comprising receiving designation of a position in at least one of the first image and the motion contrast image, wherein information on a vessel of the eye to be inspected corresponding to the designated position, which is acquired from the motion contrast image, is superimposed onto the first image for display.

6. An image display method according to claim 4, further comprising displaying a mark simultaneously indicating corresponding positions of the first image and the motion contrast image.

7. An image display method according to claim 4, further comprising simultaneously changing at least one of magnifications, displayed positions, and viewpoint positions of the first image and the motion contrast image.

8. An image display method according to claim 1, wherein the first image is generated based on an interference signal set acquired within the first area.

9. An image display method according to claim 8, wherein the interference signal set used for the generation of the first image is included in the interference signal sets corresponding to the plurality of frames.

10. An image display method according to claim 8, wherein the first image is generated by superimposing, onto one another, pieces of data of a three-dimensional tomographic image of the eye to be inspected, which are acquired from the interference signal sets corresponding to the plurality of frames.

11. An image display method according to claim 8, further comprising performing position alignment between data of a three-dimensional tomographic image of the eye to be inspected that is based on the interference signal set used for the generation of the first image and data of a three-dimensional tomographic image of the eye to be inspected that is based on an interference signal set used for the generation of the motion contrast image.

12. An image display method according to claim 11, further comprising changing a display range of the three-dimensional tomographic image in a depth direction, wherein the motion contrast image to be displayed is updated in response to the change of the display range.

13. An image display method according to claim 12, further comprising detecting layer structure of a tomographic image of the eye to be inspected from the data of the three-dimensional tomographic image,
wherein the display range is selected based on the detected layer structure.

14. An image display method according to claim 12, wherein the first image is generated by projecting and integrating pieces of data of the three-dimensional tomographic image of the eye to be inspected within the display range, and
wherein the motion contrast image that is two-dimensional, which is generated by projecting and integrating pieces of volume data of the motion contrast image in the depth direction within the display range, and the first image are displayed.

15. An image display method according to claim 14, further comprising generating, for display, a tomographic image at a position corresponding to a position designated in at least one of the first image and the two-dimensional motion contrast image, based on at least one of the data of the three-dimensional tomographic image and the volume data of the motion contrast image.

16. An image display method according to claim 8, wherein the first image comprises a motion contrast image acquired at a time different from a time when the motion contrast image is acquired.

17. An image display method according to claim 1, further comprising:
applying smoothing processing to volume data of the motion contrast image; and
applying area division processing to the volume data to which the smoothing processing has been applied.

18. An image display method according to claim 17, further comprising:
extracting, in the area division processing, a pixel that is a vessel candidate based on a pixel value indicating the volume data of the motion contrast image;
estimating a pixel having a vessel connection relationship with the pixel that is the vessel candidate; and
recognizing, as a vessel, the pixel that is the vessel candidate estimated as having the vessel connection relationship with a predetermined number or more of pixels.

19. An image display method according to claim 18, further comprising:
estimating the vessel connection relationship from the first image;
comparing connection states of the vessels with each other based on the vessel connection relationship estimated from each of the motion contrast image and the first image; and
superimposing, for display, information indicating at least a portion of the connection state of the vessel, which is a result of the comparison, onto at least one of the first image and the motion contrast image.

20. An image display method according to claim 18, further comprising:
selecting a pixel near the pixel recognized as the vessel; and
displaying a pixel estimated as having the vessel connection relationship with the selected near pixel in a manner different from the selected near pixel and a pixel near the pixel.

21. An image display method according to claim 18, further comprising:
comparing a vascular diameter calculated based on the pixel recognized as the vessel and a predetermined diameter with each other to extract a thin vessel having a diameter smaller than the predetermined diameter; and
mapping, for display, a presence ratio between a pixel recognized as the extracted thin vessel and another pixel in a predetermined area of the motion contrast image.

22. A non-transitory computer-readable storage medium having stored thereon a program for causing a computer to execute each of the steps of the image display method of claim 1.

23. An image display method according to claim 1, further comprising receiving designation of a position in at least one of the first image and the motion contrast image, wherein information on a vessel of the eye to be inspected corresponding to the designated position, which is acquired from the motion contrast image, is superimposed onto the first image for display.

24. An image display method according to claim 1, further comprising changing a display range of a three-dimensional tomographic image of the eye to be inspected in a depth direction of the eye to be inspected, the three-dimensional tomographic image being acquired from the interference signal sets corresponding to the plurality of frames,
wherein the motion contrast image to be displayed is updated in response to the change of the display range.

25. An image display method according to claim 1, further comprising generating, for display, a tomographic image at a position corresponding to a position designated in at least one of the first image and a two-dimensional motion contrast image, based on at least one of data of a three-dimensional tomographic image and volume data of the motion contrast image, the two-dimensional motion contrast image being acquired from at least a portion of the volume data in a depth direction of the eye to be inspected, the three-dimensional tomographic image being acquired from the interference signal sets corresponding to the plurality of frames.

26. An image display method according to claim 1, further comprising:
comparing a vascular diameter and a predetermined diameter with each other to extract a thin vessel having a diameter smaller than the predetermined diameter, the vascular diameter being calculated by analyzing at least one vessel in volume data of the motion contrast image; and
mapping, for display, a presence ratio between a pixel recognized as the extracted thin vessel and another pixel in a predetermined area of the motion contrast image.

27. An image display method according to claim 1, wherein the information is information on a vessel of the eye to be inspected and is acquired by analyzing at least one vessel in volume data of the motion contrast image.

28. An image display apparatus comprising:
an image acquiring unit configured to acquire a first image of a fundus within a first area of an eye to be inspected;
a signal acquiring unit configured to acquire interference signal sets corresponding to a plurality of frames, which are acquired with an intention to acquire the same cross section, for a plurality of different cross sections;
a motion contrast image generation unit configured to generate, based on the interference signal sets corresponding to the plurality of frames, a motion contrast image of the fundus within a second area included in the first area; and
a display control unit configured to superimpose, for display, information acquired from a portion of the motion contrast image of the fundus onto a corresponding position of the first image of the fundus.

29. An image display method comprising:
acquiring a first image of a fundus within a first area of an eye to be inspected;
acquiring interference signal sets corresponding to a plurality of frames, which are acquired with an intention to acquire the same cross section, for a plurality of different cross sections;
generating, based on the interference signal sets corresponding to the plurality of frames, a motion contrast image of the fundus within a second area included in the first area; and
superimposing, for display, information on a vessel of the eye to be inspected, which is extracted from one of the first image and the motion contrast image of the fundus, onto a corresponding position of another one of the first image and the motion contrast image of the fundus.

30. A non-transitory computer-readable storage medium having stored thereon a program for causing a computer to execute each of the steps of the image display method of claim 29.

31. An image display method according to claim 29, further comprising receiving designation of a position in at least one of the first image and the motion contrast image, wherein information on a vessel of the eye to be inspected corresponding to the designated position, which is acquired from the motion contrast image, is superimposed onto the first image for display.

32. An image display method according to claim 29, further comprising changing a display range of a three-dimensional tomographic image of the eye to be inspected in a depth direction, the three-dimensional tomographic image being acquired from the interference signal sets corresponding to the plurality of frames,
wherein the motion contrast image to be displayed is updated in response to the change of the display range.

33. An image display method according to claim 29, further comprising generating, for display, a tomographic image at a position corresponding to a position designated in at least one of the first image and a two-dimensional motion contrast image, based on a three-dimensional tomographic image of the eye to be inspected, the three-dimensional tomographic image being acquired from the interference signal sets corresponding to the plurality of frames, the two-dimensional motion contrast image being acquired from at least a part of the three-dimensional tomographic image in a depth direction of the eye to be inspected.

34. An image display method according to claim 29, further comprising:
comparing a vascular diameter and a predetermined diameter with each other to extract a thin vessel having a diameter smaller than the predetermined diameter, the vascular diameter being calculated by analyzing at least one vessel in volume data of the motion contrast image; and
mapping, for display, a presence ratio between a pixel recognized as the extracted thin vessel and another pixel in a predetermined area of the motion contrast image.

35. An image display method according to claim 29, wherein the information on the vessel is acquired by analyzing at least one vessel in volume data of the motion contrast image.

36. An image display apparatus comprising:
an image acquiring unit configured to acquire a first image of a fundus within a first area of an eye to be inspected;
a signal acquiring unit configured to acquire interference signal sets corresponding to a plurality of frames, which are acquired with an intention to acquire the same cross section, for a plurality of different cross sections;
a motion contrast image generation unit configured to generate, based on the interference signal set corresponding to the plurality of frames, a motion contrast image of the fundus within a second area included in the first area; and
a display control unit configured to superimpose, for display, information on a vessel of the eye to be inspected, which is extracted from one of the first image and the motion contrast image of the fundus, onto a corresponding position of another one of the first image and the motion contrast image of the fundus.

* * * * *